US009717640B1

(12) United States Patent
Pleasants

(10) Patent No.: US 9,717,640 B1
(45) Date of Patent: Aug. 1, 2017

(54) VERTEBRAL COLUMN TRACTION DEVICE AND METHOD

(71) Applicant: Donald A. Pleasants, Tampa, FL (US)

(72) Inventor: Donald A. Pleasants, Tampa, FL (US)

( * ) Notice: Subject to any disclaimer, the term of this patent is extended or adjusted under 35 U.S.C. 154(b) by 598 days.

(21) Appl. No.: 13/833,754

(22) Filed: Mar. 15, 2013

Related U.S. Application Data

(60) Provisional application No. 61/641,277, filed on May 1, 2012.

(51) Int. Cl.
*A61B 6/04* (2006.01)
*A61H 1/02* (2006.01)
*A61H 1/00* (2006.01)

(52) U.S. Cl.
CPC ............ *A61H 1/0292* (2013.01); *A61H 1/00* (2013.01)

(58) Field of Classification Search
CPC ........ A61H 1/00; A61H 1/008; A61H 1/0292; A61H 2201/0107; A61H 2201/0134; A61H 2201/0157; A61H 2201/1284; A61H 2201/1602; A61H 2201/1628; A61H 2201/163; A61H 2203/04; A61H 2203/0456; A61H 2205/088
USPC ....... 606/237–242; 128/845; 601/33, 84, 86, 601/90, 98; 5/630, 635, 648, 650
See application file for complete search history.

(56) References Cited

U.S. PATENT DOCUMENTS 1,151,894 A 8/1915 Meinecke
2,244,440 A 6/1941 Archer
3,333,286 A 8/1967 Biolik
3,389,411 A * 6/1968 Emery .............................. 5/490
3,775,785 A * 12/1973 Mittendorf ........................ 5/640
3,853,121 A * 12/1974 Mizrachy et al. .............. 601/48
4,193,150 A * 3/1980 Vineberg .......................... 5/632
4,502,170 A 3/1985 Morrow
4,777,678 A 10/1988 Moore
4,966,365 A * 10/1990 Winston ............... A63B 21/065 482/105
4,970,742 A * 11/1990 Keener ................ A47C 20/027 5/633
5,097,553 A 3/1992 Boland
5,113,875 A 5/1992 Bennett
5,306,231 A * 4/1994 Cullum et al. .................. 602/32
5,425,567 A * 6/1995 Albecker, III ......... A47C 1/146 297/377
5,887,589 A 3/1999 Hogan
6,360,387 B1 * 3/2002 Everhart .............. A47C 20/027 5/490

(Continued)

*Primary Examiner* — Steven Douglas
(74) *Attorney, Agent, or Firm* — Frijouf, Rust & Pyle, P.A.

(57) ABSTRACT

A vertebral column traction device is disclosed for expanding the vertebral column of an individual. The vertebral column traction device comprises a support body having a front surface generally adjacent to a first femur and a second femur for creating a first inclined orientation and a second inclined orientation respectively. A rear surface of the support body is distanced from a first tibia and a second tibia for creating a first cantilever orientation and a second cantilever orientation respectively. A pivot area of the support body is generally adjacent to the first tibia and the second tibia for defining a first fulcrum and a second fulcrum respectively. A first lever and the second lever are defined about the first fulcrum and the second fulcrum respectively for expanding the vertebral column.

20 Claims, 32 Drawing Sheets

(56) References Cited

U.S. PATENT DOCUMENTS

| | | | |
|---|---|---|---|
| 6,553,995 | B1 | 4/2003 | Cole et al. |
| 7,150,057 | B1 | 12/2006 | Santiago et al. |
| 8,671,480 | B1 * | 3/2014 | Leach ................................ 5/632 |
| 2003/0208846 | A1 | 11/2003 | Guarino |
| 2004/0237200 | A1 * | 12/2004 | Sells, II ............................ 5/648 |
| 2007/0094800 | A1 | 5/2007 | Hensley |
| 2012/0186587 | A1 * | 7/2012 | Steffens et al. ............... 128/845 |

* cited by examiner

VERTEBRAL COLUMN TRACTION DEVICE AND METHOD

CROSS-REFERENCE TO RELATED APPLICATIONS

This application claims benefit of U.S. Patent Provisional application No. 61/641,277 filed May 1, 2012. All subject matter set forth in provisional application No. 61/641,277 is hereby incorporated by reference into the present application as if fully set forth herein.

BACKGROUND OF THE INVENTION

Field of the Invention

This invention relates to traction and more particularly to a vertebral column traction device for expanding the vertebral column of an individual.

Background of the Invention

It has been estimated that between sixty and eighty percent of the population will experience back pain at some point during their lives. Common causes for back pain include nerve and muscular problems, as well as degenerative disc disease. Mechanical back problems are due to the way a person's spine moves in relation to certain body movements.

One of the most common mechanical causes of back pain is intervertebral disc degeneration which is the deterioration of discs located between the vertebrae with age. The resultant loss of cushioning ability can lead to back pain if the back is stressed. Spinal injuries such as sprains or fractures can cause either short term or chronic back pain.

Lower back pain due to muscle strain will eventually affect a high percentage of the population at some time during their life. The series of muscles and ligaments in the back of a person maintain the proper alignment of the spinal column. Stretching these muscles beyond their normal extension results in small tears in the muscle tissue. The muscles are resultantly weakened and may not maintain proper spinal alignment. The less stable spinal column results in lower back pain. Lower back pain can result from a multitude of causes. Extreme physical exertion, falling, lifting heavy objects or bending are just a few of the possible causes of lower back pain.

Recommended treatment for lower back pain includes bed rest and stretching. Placing a pillow under the knees of a patient lying on his/her back has been suggested to help aiding in the alleviation of back pain. Several types of traction devices have been developed to assist the patient with stretching back muscles in an effort to relieve back pain.

There have been many in the prior art who have attempted to solve these problems with varying degrees of success. None, however completely satisfies the requirements for a complete solution to the aforestated problem. The following U. S. Patents are attempts of the prior art to solve this problem.

U.S. Pat. No. 1,151,894 to Meinecke discloses a bed rest having a base provided with slots and strips of non-slipping material held by the slots. The base is provided with a group of parallel slots on each side thereto and a strip of non-slipping material laced in and out of each group of slots and held thereby.

U.S. Pat. No. 244,480 to Archer discloses a combination leg and back rest with spaced upright front and rear leg members, and a body member support comprising spaced side rail members is rigidly connected at the ends thereof to the upper ends of the front and rear leg members and a cover member extending between and secured to the side rails. The support extends downwardly from the upper ends of the rear legs at a sharp angle thereto. A rocking bearing member is secured to the lower ends of the rear leg members. The relative dimensions of and the angular relation between the legs and the support is such that when the rest is tilted about the bearing member to dispose said support in substantially horizontal position, substantially the entire weight of the rest will be balanced on the bearing member.

U.S. Pat. No. 3,333,286 to Biolik discloses an adjustable sick-bed, bolster, comprising at least two bolster sections with its longitudinal section of a substantially trapeziform. The bolster has a horizontal base surface, a shorter horizontal top surface, a vertical rear-end surface, and an inclined front-end surface extending at an angle from the front end of the base surface to the front end of the top surface. The bolster is divided into at least two wedge shaped bolster sections along a partition plane extending from a horizontal centerline of the inclined front-end surface in an angular upward direction to an upper rear edge line of the vertical rear-end surface. The lower of the bolster sections has a trapeziform longitudinal section and the upper of the bolster sections has a substantially triangular longitudinal section.

U.S. Pat. No. 3,853,121 to Mizrachy, et al. discloses a method for reducing the risk of incurring venous thrombosis in operative and post-operative patients. Vibration and/or massage is imparted to the legs of a patient during and after surgery. The vibration and/or massage aids muscular activity in the legs, which in turn stimulates the blood vessels reducing the probability of formation of a blood clot therein.

U.S. Pat. No. 4,502,170 to Morrow discloses a method for improving posture and relieving back pain of a person in a supine position. The invention includes the steps of pressing a convex pillow against the region of the ilia, sacrum, and fifth lumbar vertebra to produce a substantial sacral base angle and to fully oppose any moment tending to cause rotational shifting of the pelvis, and supporting the thighs and calves in an elevated position such that the thighs extend upwardly at an angle of from about 53 degrees to 63 degrees from horizontal. The calves extend at an angle of from about 0 degrees to 20 degrees downwardly from horizontal. The method normally also includes simultaneously resiliently supporting the back of the neck in an elevated position while permitting the cervical vertebrae to maintain their normal, physiologic curvature, in supporting the head of the person in an elevated position while maintaining the cervical vertebrae and the occiput in an unflexed, physiologic position.

U.S. Pat. No. 4,777,678 to Moore discloses a method and apparatus for providing orthopedic support. A preferred system includes a pair of wedge-shaped pillows, a cervical pillow and a rectangular elevation pillow. The pillows can be made of polyurethane foam and covered with nylon. One of the wedge-shaped pillows has a cross-section of a right isosceles triangle. The other wedge-shaped pillow also has a cross-section substantially similar to a right isosceles triangle but has a concave portion suitable for receiving a convex neck support area of the cervical pillow. The pillows preferably include Velcro™ strips which allow the pillows to be interconnected and connected to a mat so that an individual's legs and head can be appropriately supported to induce a pain-reducing curve in the individual's lower back. Rings are attached to the sides of pillows. Velcro™ covered straps adjustably interconnect the rings to allow for various adjustable arrangements of the pillows. When the pillows are not in use to provide orthopedic support, they can be combined to form a geometric solid, e.g. a cube. Thus, they can be readily stored and transported in a compact solid shape, and can also be used as a small chair, stool or ottoman.

U.S. Pat. No. 5,097,553 to Boland discloses a device for supporting one's thighs, knees, calves, and feet to obtain relief and comfort from low back pain. The device permits the user to be placed in the correct position to strengthen the stomach muscles without risking injury to the back. When a prone user disposes his thighs at a 32 degree angle to the vertical, the lower spine is partially flattened and the lower back muscle tension is reduced. The curved areas of the support under the knees and heels, and in the same horizontal plane, provide a comfortable transition from the thigh supporting surfaces to the calf and foot supporting areas. The horizontal surface is depressed intermediate to its length and creates a final subtle incline to receive the calf muscles. The unit is customized to the user's leg length measurements.

U.S. Pat. No. 5,113,875 to Bennett discloses an inflatable leg-supporting bolster including a pair of flexible side panels joined to opposite side edges of a connecting flexible sheet that encircle them. A horizontal web and a plurality of upright webs are provided at the interior of the bolster to define lateral and upright configurations required for proper leg support when used by a person lying in a supine position.

U.S. Pat. No. 5,887,589 to Hogan discloses a skeletal realignment system which is specifically designed to alleviate man) of the back aches and pains that are a direct result of a skeletal misalignment. The system consists of a first implement and an identical second implement. To use the system, the two implements are positioned side-by-side on a flat surface, such as a floor mat, with one of the implements rotated 180 degrees from the other. The back of a person is then positioned over the implements and a short exercise is performed until the back is realigned at which time the person carefully rises to a standing position.

U.S. Pat. No. 6,553,995 to Cole, et al. discloses a patient positioning kit comprising a set of vinyl-coated polyurethane foam forms and storage unit. The kit functions to support injured patient extremities during specific surgical procedures. The kit may be tailored to certain surgical specialties such as orthopedic traumatology or orthopedic sports medicine. For the given surgical specialty, each kit is composed of foam forms specifically for the most often performed surgical procedures within that specialty. Each kit contains a significant variety of support pieces such that various patient sizes and extremity positions may be stabilized. Both arm and leg associated procedures are facilitated by component pieces of the patient positioning kit. The kit pieces are coated with a polymeric material that forms a protective shell that increases piece durability and reduces fluid uptake.

U.S. Pat. No. 7,150,057 to Santiago, et al. discloses a pillow approximately like the letter P in a prone position with a substantially flat or even top or upper surface that upwardly underlies the lower legs, beginning from the calves towards the heels, of the supine user to relieve stress or leg fatigue from long hours of work, shopping, standing or walking, to improve blood circulation and to help prevent varicose veins. It is made of spongy or resilient material, and covered by an inner overlay as a lining and a replaceable outer outlay as a pillowcase. It is intended for use at home, office or any room or place with adequate space.

United States Patent Application number 2003/0208846 to Guarino discloses a single piece, multi-use support pillow with curved ends of varying heights and dual inclined support surfaces designed to contour and support differing parts of a human body, which helps to maintain proper body alignment with even distribution of weight throughout muscular/skeletal system of an individual. The support pillow provides support with a contour fit for potentially all of the following areas: head, neck, shoulders, torso, back, thighs, knees, shins, ankles, feet, and toes.

United States Patent Application number 2007/0094800A to Hensley discloses a therapeutic support configured to support the legs of the user for use when lying on a generally flat surface such as a bed or the like to relieve lower back pain. The support includes an apex and a flat base, the apex having a groove therein and side wings to prevent the user's legs from sliding out of the groove. The support promotes a posture in which the lower back and the feet are flat on the bed surface and the vertebrae of the spine are in a physiologically neutral position.

Although the aforementioned prior art have contributed to the development of the art of securing an object to a support member, none of these prior art patents have solved the needs of this art.

Therefore, it is an object of the present invention to provide an improved apparatus for providing support and traction to the back of a patient lying on a planar surface.

Another object of this invention is to provide an improved method of establishing traction to the spine of a patient lying on a planar surface.

Another object of this invention is to provide an improved apparatus that is simple for the patient to use.

Another object of this invention is to provide an improved apparatus that is easy to cost effectively produce.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an improved apparatus and method for expanding the vertebral column of an individual. The vertebral column extends between an upper column end and a lower column end. The vertebral column includes a plurality of vertebrae separated by a plurality of intervertebral discs. A pelvis is coupled to the lower column end of the vertebral column. A first femur and a second femur extend between a proximal end and a distal end. The proximal end of the first femur and the second femur are coupled to the pelvis. A first tibia and a second tibia extend between a proximal end and a distal end. The proximal end of the first tibia and the second tibia are coupled to the distal end of the first femur and the second femur by a first knee joint and a second knee joint respectively. A first foot and a second foot are coupled to the distal end of the first tibia and the second tibia respectively. A support surface has a generally horizontal surface for supporting a portion of the individual and a generally vertical surface for extending a portion of the individual beyond the support surface. The vertebral column traction device comprises a support body including a base plane surface, an inclined plane surface, a riser plane surface, a first triangle plane surface and a second triangle plane surface for defining a generally shaped wedge. The base plane surface intersects the inclined plane surface for defining a first vertex. The inclined plane surface intersects the riser plane surface for defining a second vertex. The riser plane surface intersects the base plane surface for defining a third vertex. The base plane surface is adjacent to the generally horizontal surface and the riser plane surface is in proximity with the generally vertical surface of the support surface for defining an operation position of the support body. The inclined plane surface is generally adjacent to the first femur and the second femur for positioning the first femur and the second femur in a first inclined orientation and a second inclined orientation respectively. The riser plane surface is distanced from the first tibia and the second tibia for positioning the first tibia and the second tibia in a first cantilever orientation and a second cantilever orientation respectively. The second vertex is generally adjacent to the first tibia and the second tibia and the first tibia and the second tibia are pivoting on the second vertex for defining a first fulcrum and a second fulcrum respectively. The first fulcrum and the first knee joint define a first distance. The first distance has a first mass. The first fulcrum and the first foot define a second distance. The second distance has a second mass. The second fulcrum and the second knee joint define a third distance. The third distance has a third mass. The second fulcrum and the second foot define a fourth distance. The fourth distance has a fourth mass. The second distance is greater than the first distance for defining a first lever about the first fulcrum. The fourth distance is greater than the third distance for defining a second lever about the second fulcrum. The second mass is greater than the first mass for creating a primary mechanical advantage output force from the first lever including a first ascending vertical force and a first distal horizontal force in the first distance. The primary mechanical advantage output force is conveyed from the first femur, through the pelvis and to the vertebral column for expanding the vertebral column of an individual. The fourth mass is greater than the third mass for creating a secondary mechanical advantage output force from the second lever including a second ascending vertical force and a second distal horizontal force in the third distance. The secondary mechanical advantage output force is conveyed from the second femur, through the pelvis and to the vertebral column for expanding the vertebral column of an individual.

In a more specific embodiment of the invention, a braking body extends from the base plane surface for positioning adjacent to the generally vertical surface of the support surface for preventing a horizontal displacement of the support body relative to the support surface.

In an another embodiment of the invention, a first supplementary weight is coupled to the first tibia or the first foot for increasing the second mass and increasing the primary mechanical advantage output force to further expand the vertebral column of the individual. A second supplementary weight is coupled to the second tibia or the second foot for increasing the fourth mass and increasing the secondary mechanical advantage output force to further expand the vertebral column of the individual.

The invention is also incorporated into the method comprising the steps of positioning a generally shaped wedge support body adjacent to a generally horizontal surface and in proximity with a generally vertical surface of a support surface. A first femur and a second femur are positioned adjacent to an inclined plane surface of the generally shaped wedge support body for placing the first femur and the second femur in a first inclined orientation and a second inclined orientation respectively. A first tibia and a second tibia are positioned so that there is a distance between the first tibia and the second tibia from a riser plane surface of the generally shaped wedge support body for positioning the first tibia and the second tibia in a first cantilever orientation and a second cantilever orientation respectively. The first tibia and the second tibia are positioned adjacent to a vertex between the inclined plane surface and the riser plane for pivoting the first tibia and the second tibia on the vertex for defining a first fulcrum and a second fulcrum respectively. A first lever is created about the first fulcrum. A second lever is created about the second fulcrum. A primary mechanical advantage output force is generated by the first lever and is conveyed from the first femur, through the pelvis and to the vertebral column for expanding the vertebral column of an individual. A secondary mechanical advantage output force is generated by the second lever and is conveyed from the second femur, through the pelvis and to the vertebral column for expanding the vertebral column of an individual.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which.

Similar reference characters refer to similar parts throughout the several Figures of the drawings.

DETAILED DISCUSSION

Description of Anatomy

Figure 1:
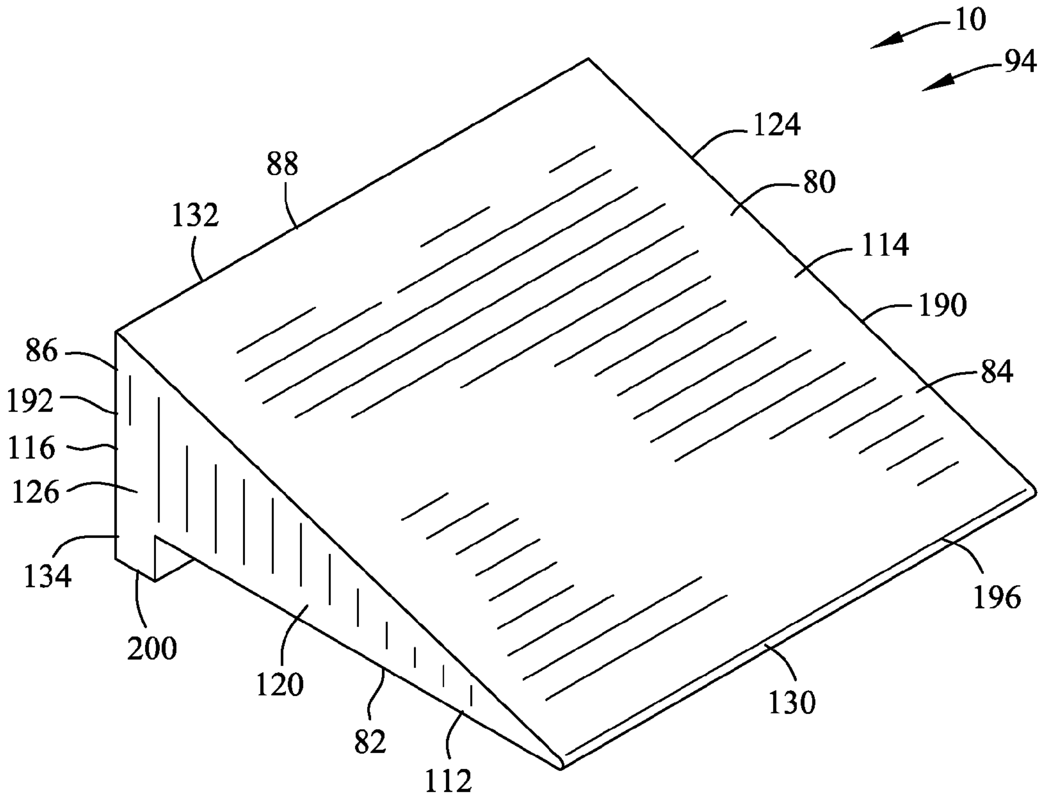
FIG. 1 is a top isometric view of a vertebral column traction device for expanding the vertebral column of an individual.
Figure 2:
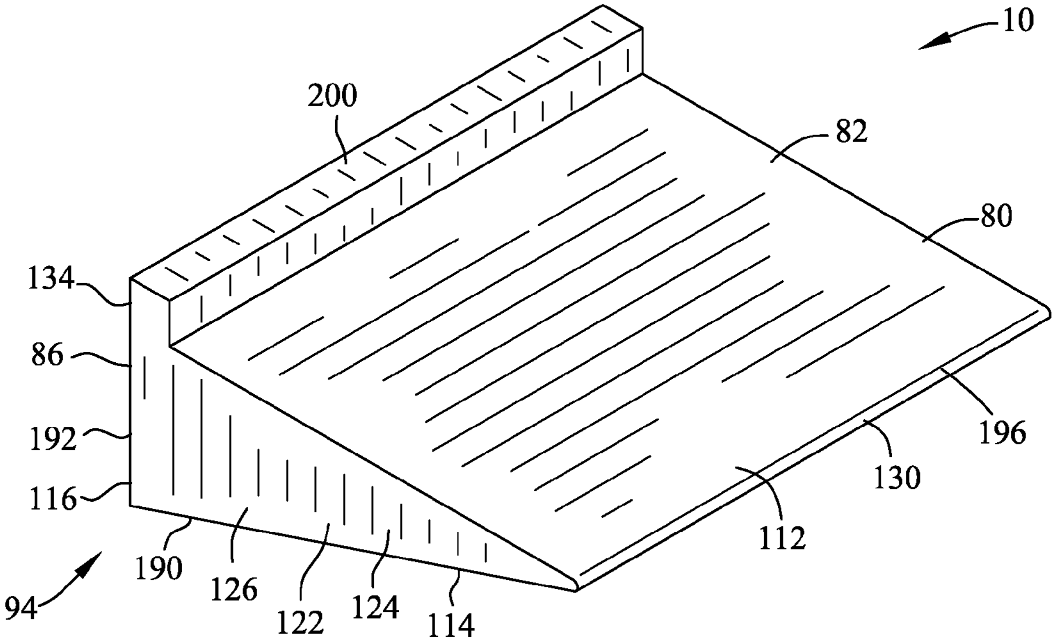
FIG. 2 is a bottom isometric of FIG. 1.
Figure 3:
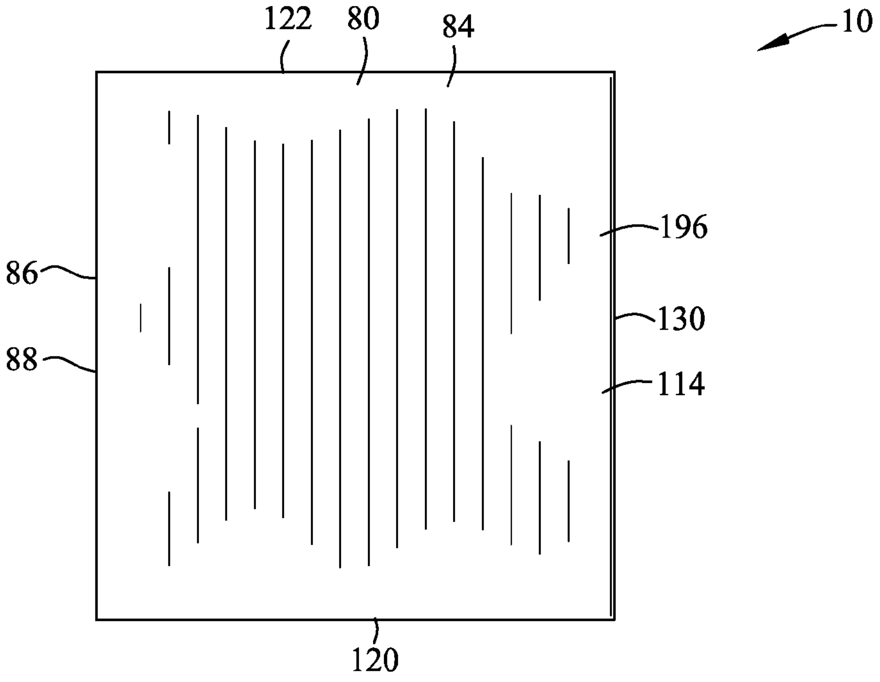
FIG. 3 is a top view of FIG. 1.
Figure 4:
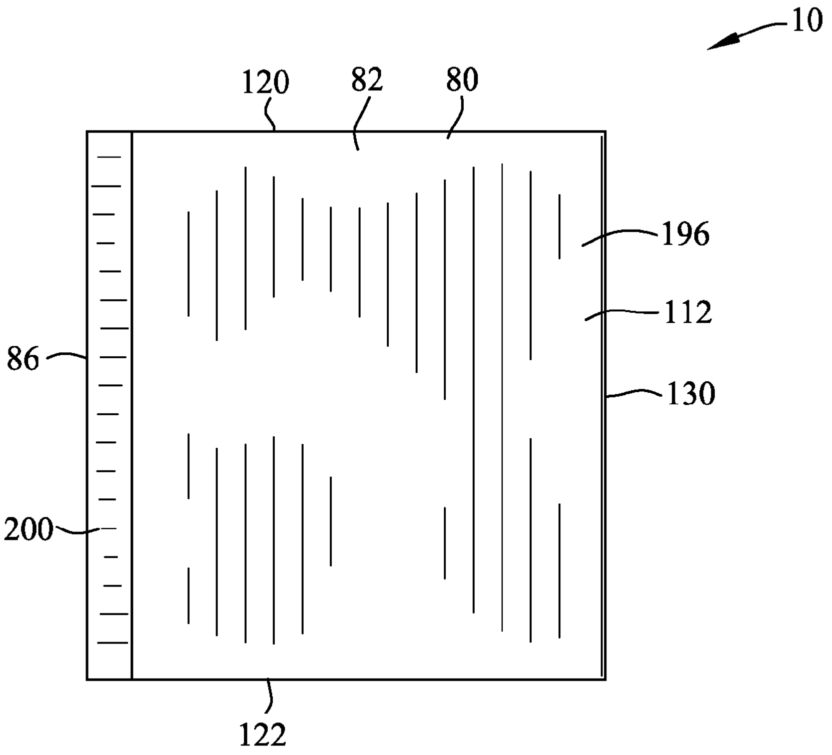
FIG. 4 is a bottom view of FIG. 1.
Figure 6:
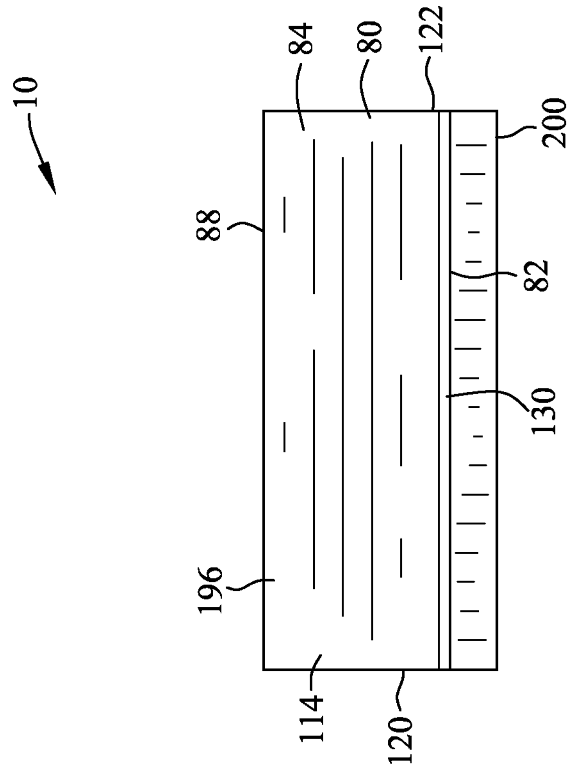
FIG. 6 is a front view of FIG. 1.
Figure 5:
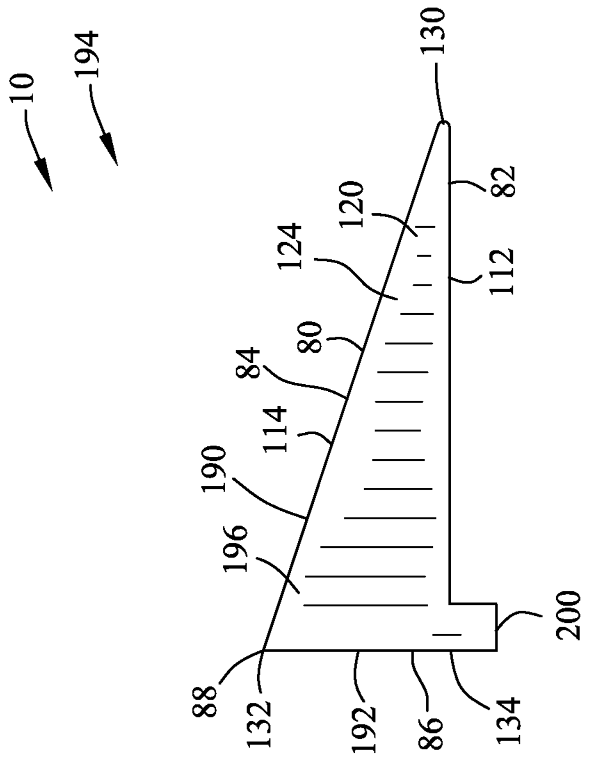
FIG. 5 is a side view of FIG. 1.
Figure 7:
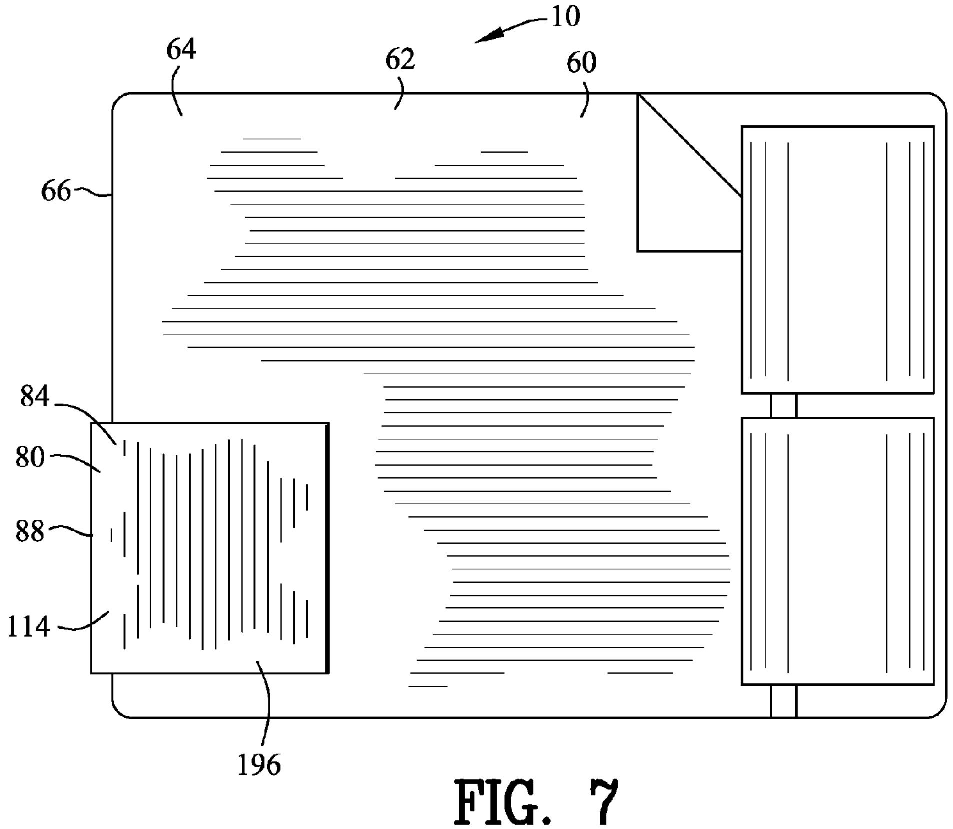
FIG. 7 is a view similar to FIG. 3 illustrating a support body positioned on a support surface in an operation position.
Figure 8:
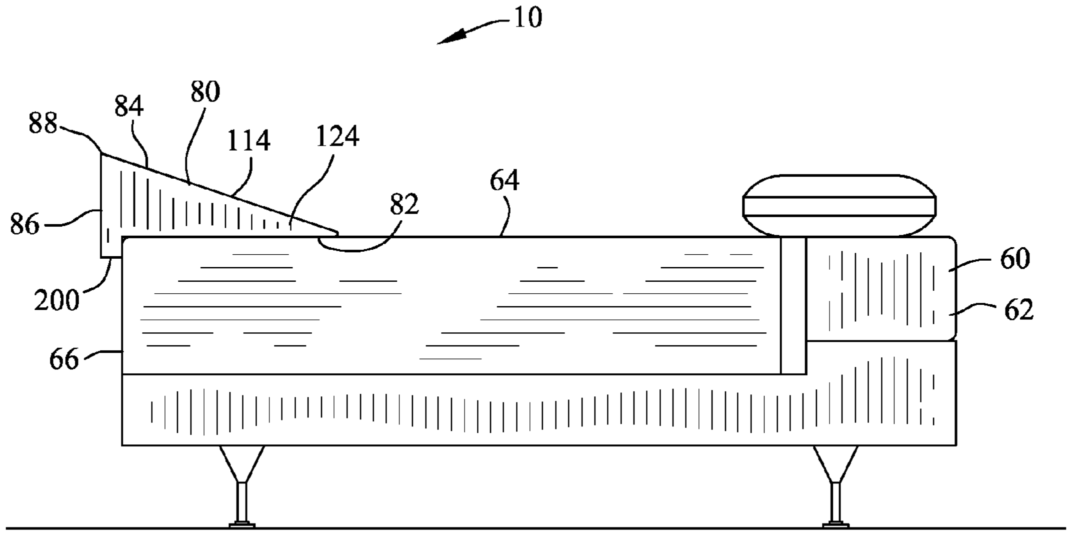
FIG. 8 is a side view of FIG. 7.

FIGS. 1-8, 11, 13-15 and 17 are various views of a vertebral column traction device 10 for expanding the vertebral column 20 of an individual 12. The vertebral column traction device 10 also releases pressure between the vertebral column 20 of an individual 12. As best shown in FIGS. 9-12 and 15-18, the vertebral column 20 extends between an upper column end 22 and a lower column end 24. The vertebral column 20 includes a plurality of vertebrae 26 separated and kept apart by a plurality of intervertebral discs 28. Each of the plurality of vertebrae 26 include a foramen transversium 13. The foramen 13 are the areas or spaces or "openings" between the vertebrae 26 where nerves 14 exit the spinal canal 16 and run down to the legs 31 and 33, in the case of the lumbar spine 17.

A pelvis 30 is coupled to the lower column end 24 of the vertebral column 20. A first leg 31 and a second leg 32 include a first femur 32 and a second femur 34 extend between a proximal end 36 and a distal end 38 respectively. The proximal end 36 of the first femur 32 and the second femur 34 are coupled to the pelvis 30. A first tibia 40 and a second tibia 42 extend between a proximal end 44 and a distal end 46. The proximal end 44 of the first tibia 40 and the second tibia 42 are coupled to the distal end 38 of the first femur 32 and the second femur 34 by a first knee joint 50 and a second knee joint respectively 52. The first leg 31 includes a first upper limb 48 and a first lower limb 49. The second leg 32 includes a second upper limb 58 and a second lower limb 59. A first foot 54 and a second foot 56 are coupled to the first lower limb 49 and a second lower limb 59 respectively.

Description of Condition

During the course of the day and especially where the individual 12 is in the upright position for long periods of time, the plurality of vertebrae 26 may compress against the plurality of intervertebral discs 28. The compression of the plurality of intervertebral discs 28 forces bodily fluids from the plurality of intervertebral discs 28. If the compression of the plurality of intervertebral discs 28 persists many medical conditions may result including but not limited to spinal stenosis.

Figure 9:
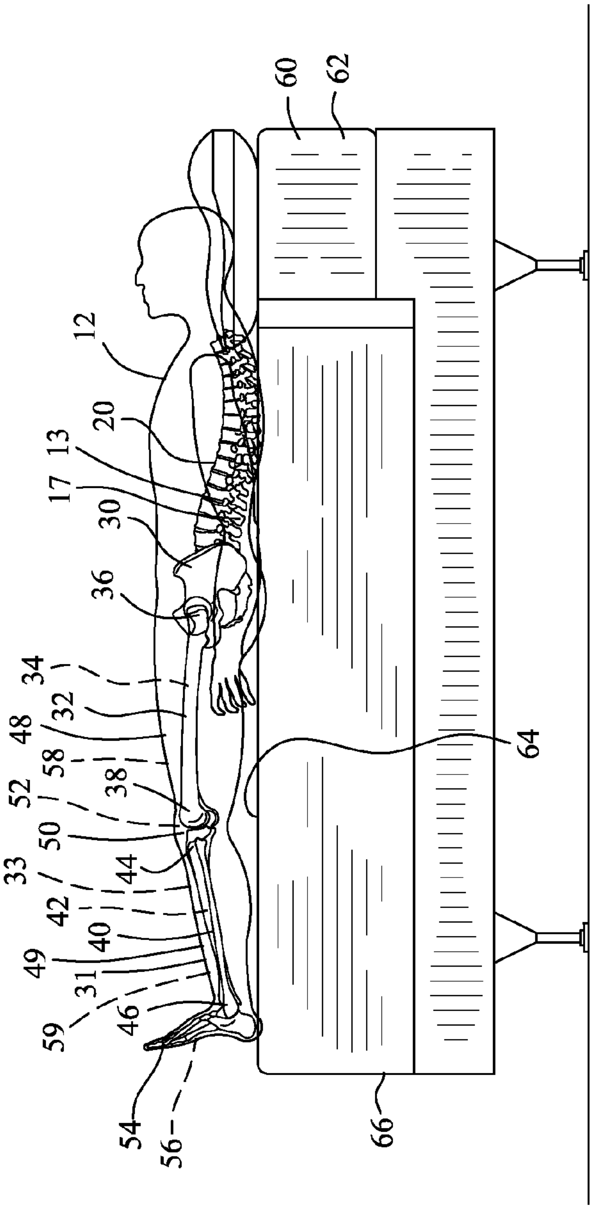
FIG. 9 is a view similar to FIG. 8 with an individual lying on the support surface body without the vertebral column traction device.
Figure 10:
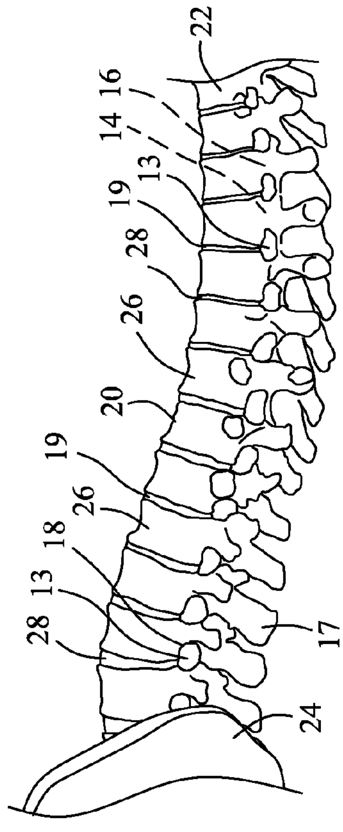
FIG. 10 is an enlarge view of a portion of FIG. 9 illustrating a non-expanded vertebral column.
Figure 11:
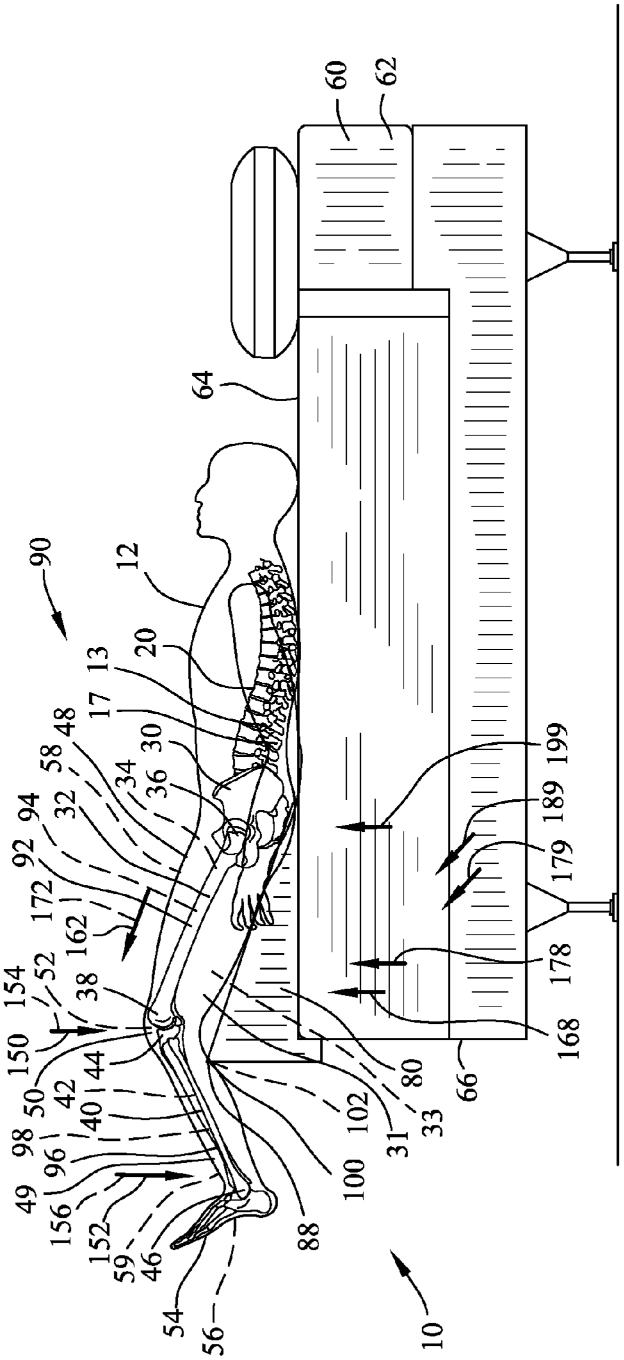
FIG. 11 is a view similar to FIG. 8 with an individual lying on the support surface body and utilizing vertebral column traction device of FIG. 1.
Figure 12:
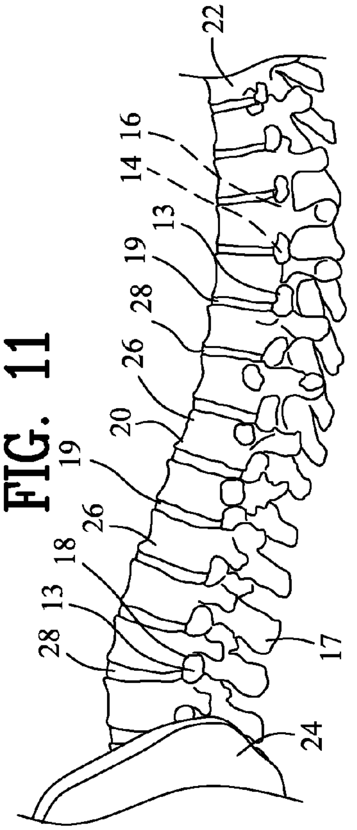
FIG. 12 is an enlarge view of a portion of FIG. 11 illustrating an expanded vertebral column.

As shown in FIGS. 9 and 10, if the intervertebral discs deteriorate or become dried out, the foramen 13 or space between the intervertebral discs 28 becomes narrower. As the space between the intervertebral discs 28 becomes narrower it frequently impinges on the nerve 14 exiting the spinal canal 16, often called the "nerve root" 18. The nerve root 18 then frequently swells with normal irritation, making it larger and even more susceptible to coming in contact with the bony vertebrae 26 above and below the nerve root 18, causing an undesirable cycle of continuing irritation and resulting leg pain. The narrowing of the intervertebral space 19 occupied by the intervertebral discs 28 is called spinal stenosis, and is a common finding in cases of lumbar back and leg complaints.

As shown in FIGS. 11, 12, 15, 16, 17 and 18, in order to promote hydration of the plurality of intervertebral discs 28 and potentially avoid spinal stenosis, the vertebral column 20 may be exposed to an expanding force or a releasing pressure between the vertebral column 20 of an individual 12. More specifically, the expansion of the plurality of intervertebral discs 28 may prompt bodily fluids back into the plurality of intervertebral discs 28 and thus alleviate spinal stenosis. The vertebral column traction device 10 is intended to be utilized for a portion of the day in order to expand the vertebral column and promoting rehydration of the plurality of intervertebral discs 28 and thus alleviate spinal stenosis and other spinal ailments.

Description of Device

As shown in FIGS. 7-9, 11, 15 and 17, the vertebral column traction device 10 is positioned upon a support surface 60. The support surface 60 is shown as a bed 62, however the support surface 60 may alternatively include a table, bench or other horizontal surface. The support surface 60 has a generally horizontal surface 64 for supporting a portion of the individual 12 and a generally vertical surface 66 for extending a portion of the individual 12 beyond the support surface 60.

The vertebral column traction device 10 comprises a support body 80 including a base surface 82, a front surface 84 and a rear surface 86. The front surface 84 intersects the rear surface 86 for defining a pivot area 88. The base surface 82 is positioned adjacent to the generally horizontal surface 64 and the rear surface 86 is positioned in proximity with the generally vertical surface 66 of the support surface 60 for defining an operation position 90 of the support body 80.

The front surface 84 is generally adjacent to the first femur 32 and the second femur 34 for positioning the first femur 32 and the second femur 34 in a first inclined orientation 92 and a second inclined orientation 94 respectively. The rear surface 86 is distanced from the first tibia 40 and the second tibia 42 for positioning the first tibia 40 and the second tibia 42 in a first cantilever orientation 96 and a second cantilever orientation 98 respectively. The pivot area 88 is generally adjacent to the first tibia 40 and the second tibia 42 and the first tibia 40 and the second tibia 42 pivoting on the pivot area 88 for defining a first fulcrum 100 and a second fulcrum 102 respectively.

Alternatively, the vertebral column traction device 10 may comprises a support body 80 including base plane surface 112, an inclined plane surface 114, a riser plane surface 116, a first triangle plane surface 120 and a second triangle plane surface 122 for defining a generally shaped wedge 124. The base plane surface 112 intersects the inclined plane surface 114 for defining a first vertex 130. The inclined plane surface 114 intersects the riser plane surface 116 for defining a second vertex 132. The riser plane surface 116 intersects the base plane surface 112 for defining a third vertex 134.

The base plane surface 112 is adjacent to the generally horizontal surface 64 and the riser plane surface 116 is in proximity with the generally vertical surface 66 of the support surface 60 for defining the operation position 90 of the support body 80. The inclined plane surface 114 is generally adjacent to the first femur 32 and the second femur 34 for positioning the first femur 32 and the second femur 34 in the first inclined orientation 92 and the second inclined orientation 94 respectively. The riser plane surface 116 is distanced from the first tibia 40 and the second tibia 42 for positioning the first tibia 40 and the second tibia 42 in the first cantilever orientation 96 and the second cantilever orientation 98 respectively. The second vertex 132 is generally adjacent to the first tibia 40 and the second tibia 42 and the first tibia 40 and the second tibia 42 are pivoting on the second vertex 132 for defining the first fulcrum 100 and a second fulcrum 102 respectively.

The first fulcrum 100 and the first knee joint 50 define a first distance 140. The first distance 140 has a first mass 150. The first fulcrum 100 and the first foot 54 define a second distance 142. The second distance 142 has a second mass 152. The second fulcrum 102 and the second knee joint 52 define a third distance 144. The third distance 144 has a third mass 154. The second fulcrum 102 and the second foot 56 define a fourth distance 146. The fourth distance 146 has a fourth mass 156.

The second distance 142 is greater than the first distance 140 for defining a first lever 160 about the first fulcrum 100. The fourth distance 146 is greater than the third distance 144 for defining a second lever 170 about the second fulcrum 102.

The second mass 152 is greater than the first mass 150 for creating a primary mechanical advantage output force 162 from the first lever 160 including a first ascending vertical force 164 and a first distal horizontal force 166 in the first distance 140. The primary mechanical advantage output force 162 is conveyed from the first femur 32, through the pelvis 30 and to the vertebral column 20 for expanding the vertebral column 20 of an individual 12.

Figure 19:
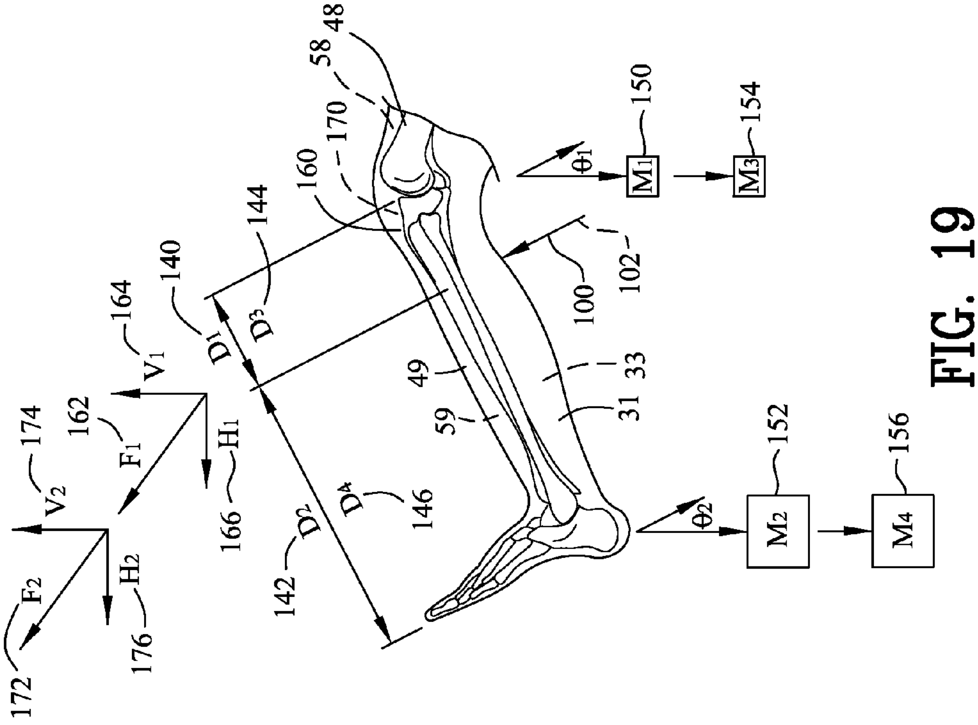
FIG. 19 is an enlarged view of a portion of FIG. 11 illustrating a first lever and a second lever.
Figure 21:
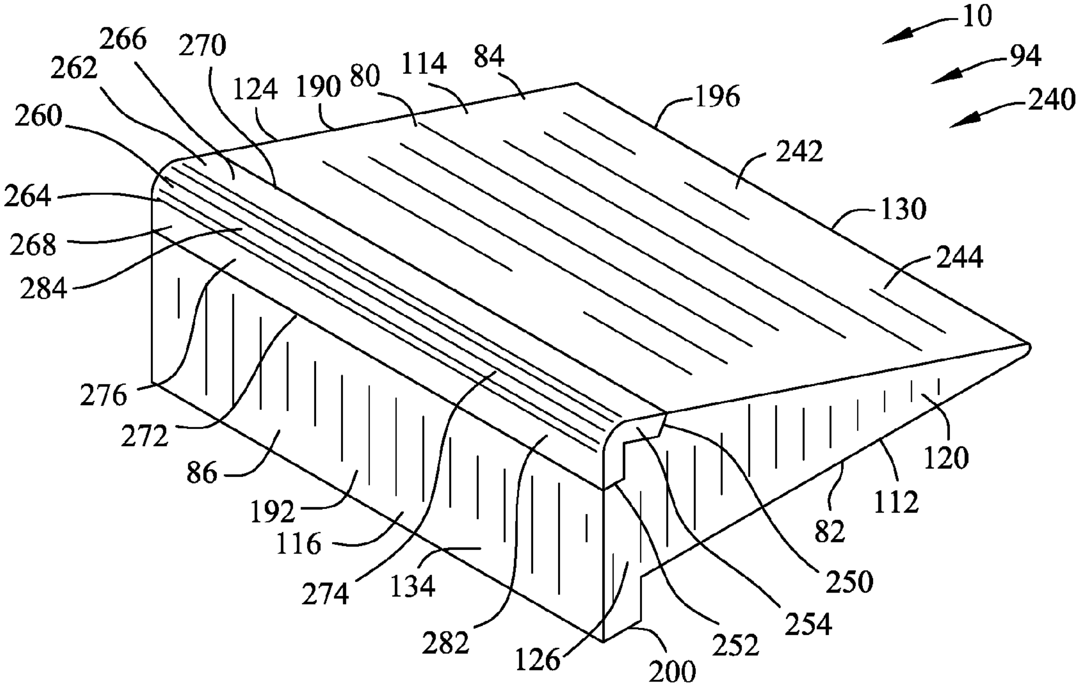
FIG. 21 is a top isometric view of a third embodiment of the vertebral column traction device for expanding the vertebral column of an individual wherein the pivot area includes a supplemental support layer positioned within a groove.
Figure 22:
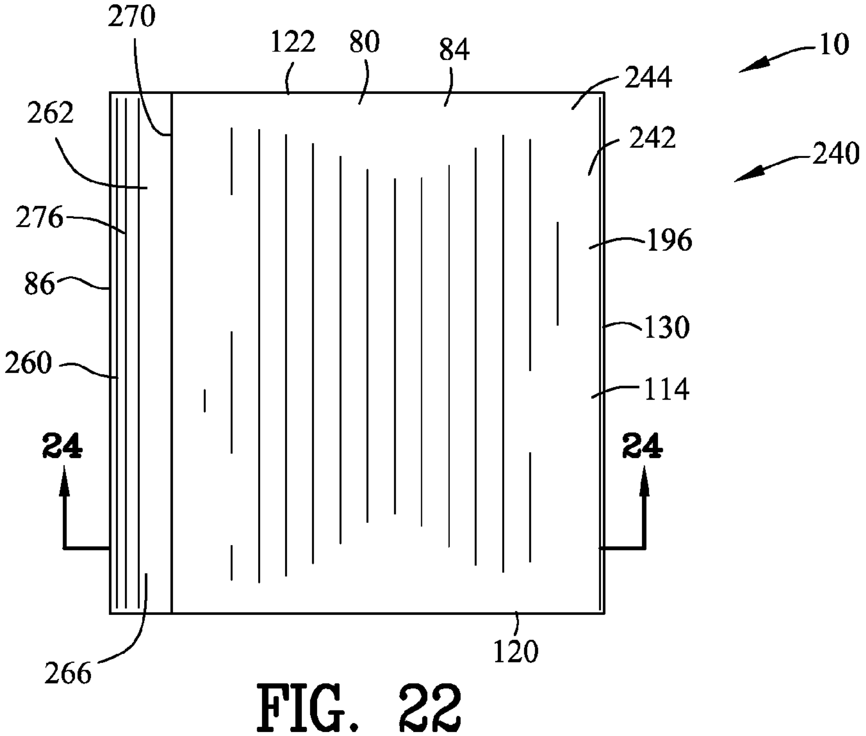
FIG. 22 is a top view of FIG. 21.
Figure 23:
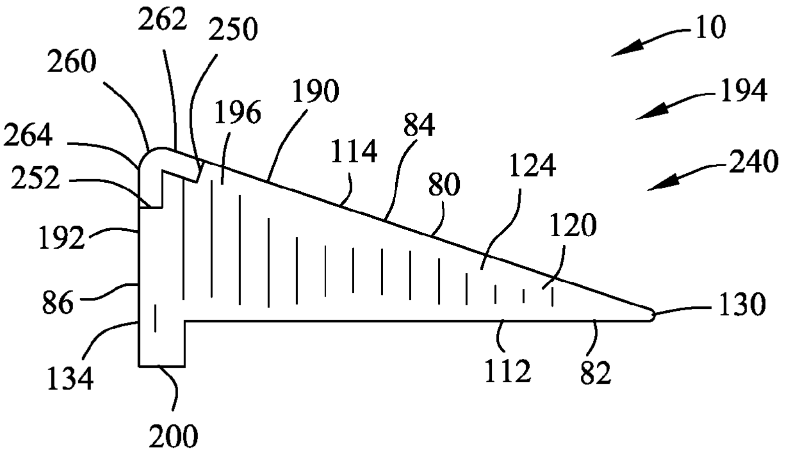
FIG. 23 is a side view of FIG. 21.
Figure 24:
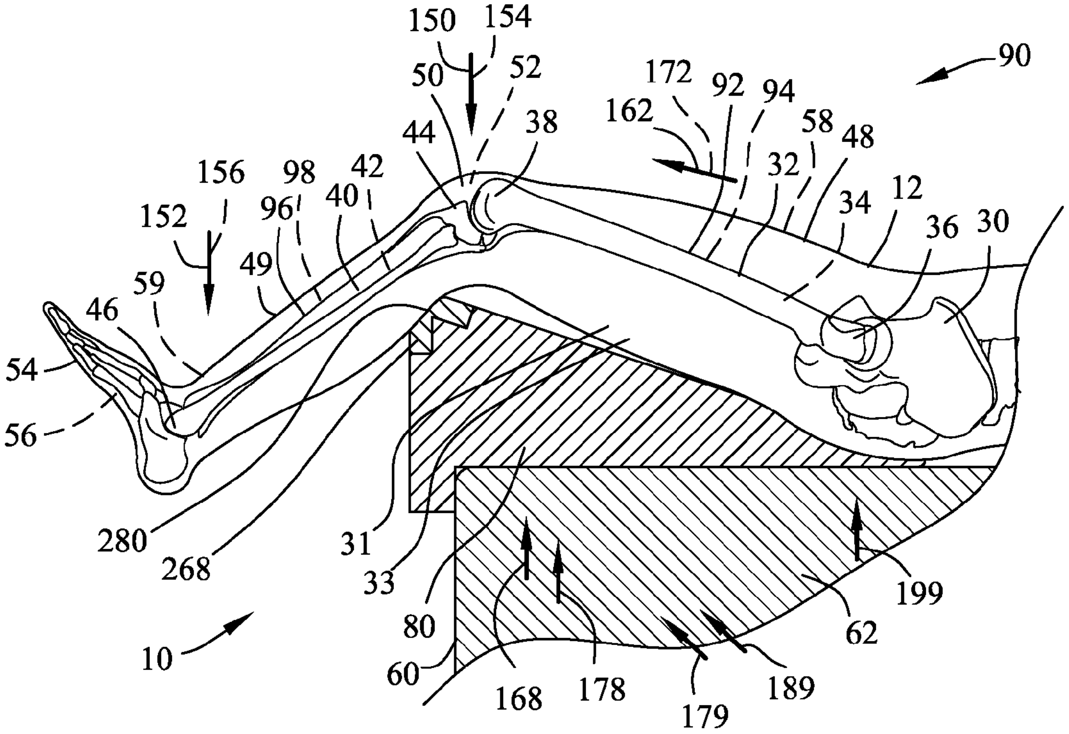
FIG. 24 is a sectional view along line 24-24 in FIG. 22 illustrating the supplemental support layer permitting an increased displacement for increasing the surface area between the first femur and the second femur for increasing comfort and preventing body circulation problems.
Figure 25:
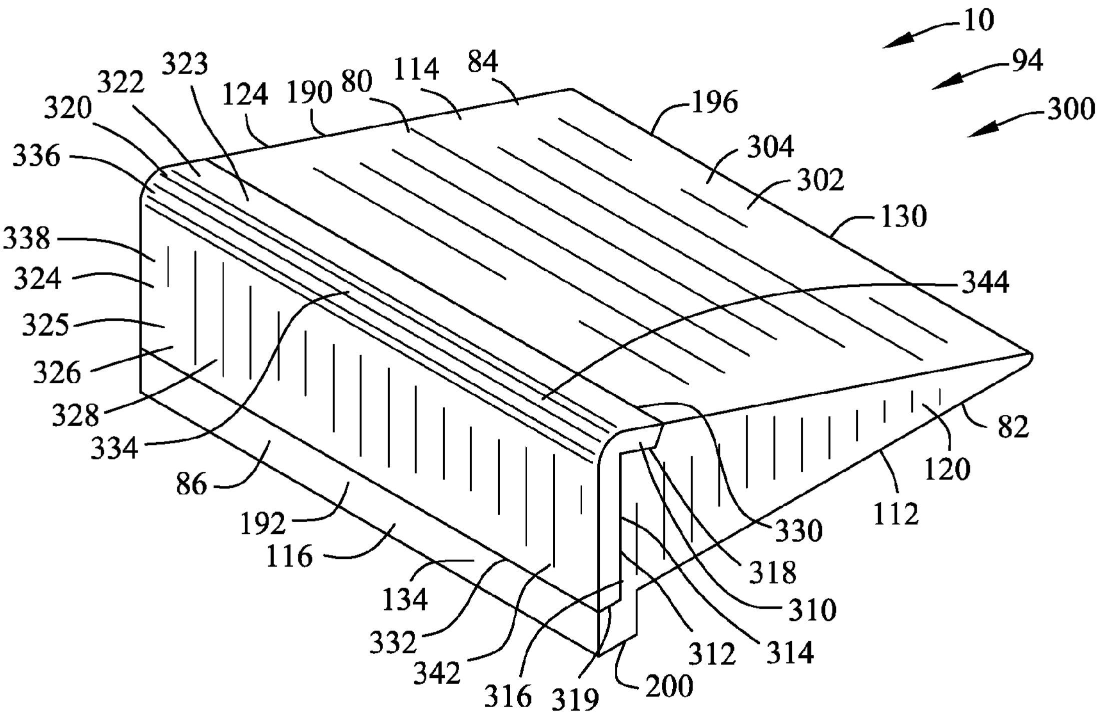
FIG. 25 is a top isometric view of a fourth embodiment of the vertebral column traction device for expanding the vertebral column of an individual wherein the pivot area includes a supplemental support layer positioned within a groove.
Figure 26:
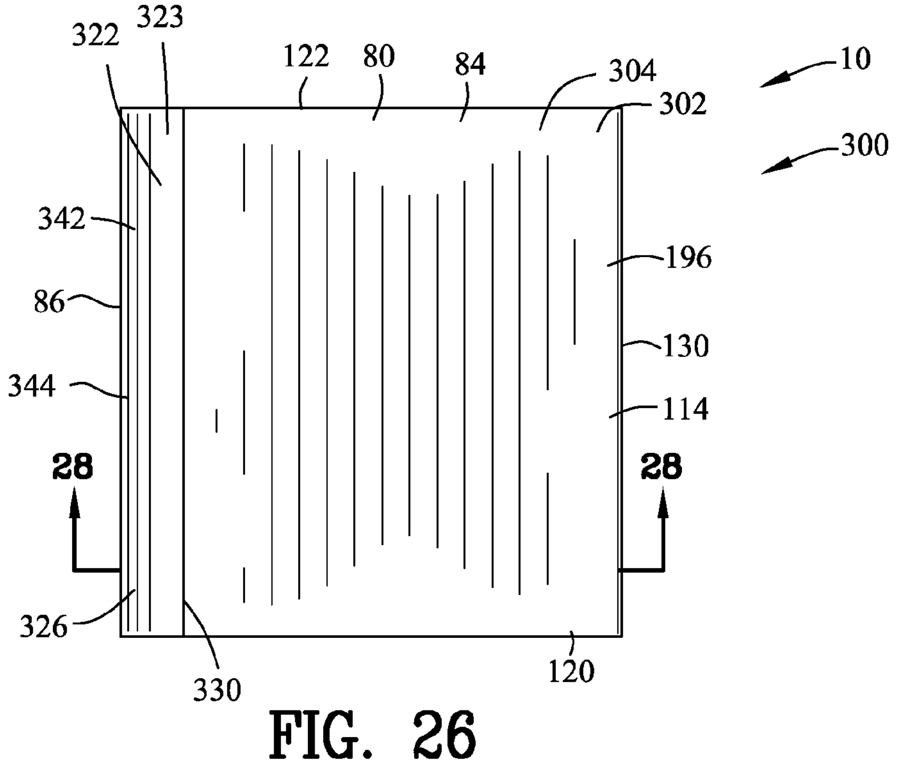
FIG. 26 is a top view of FIG. 25.
Figure 27:
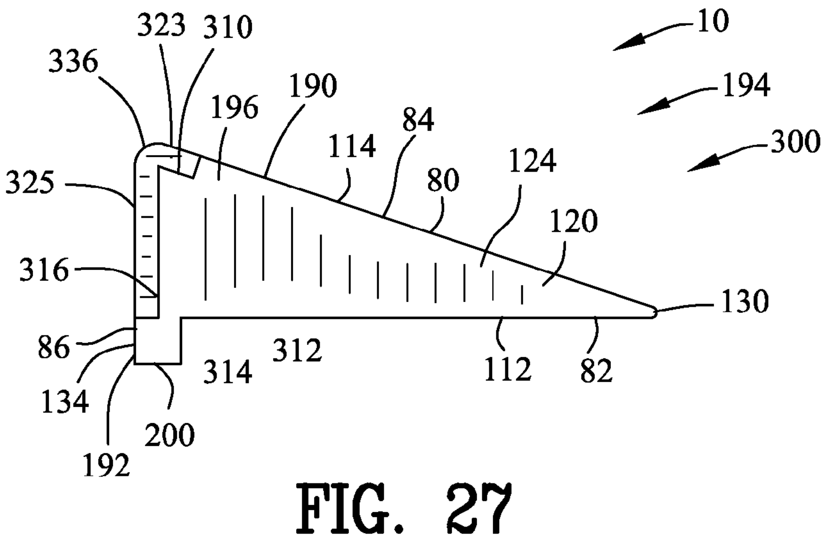
FIG. 27 is a side view of FIG. 25.
Figure 28:
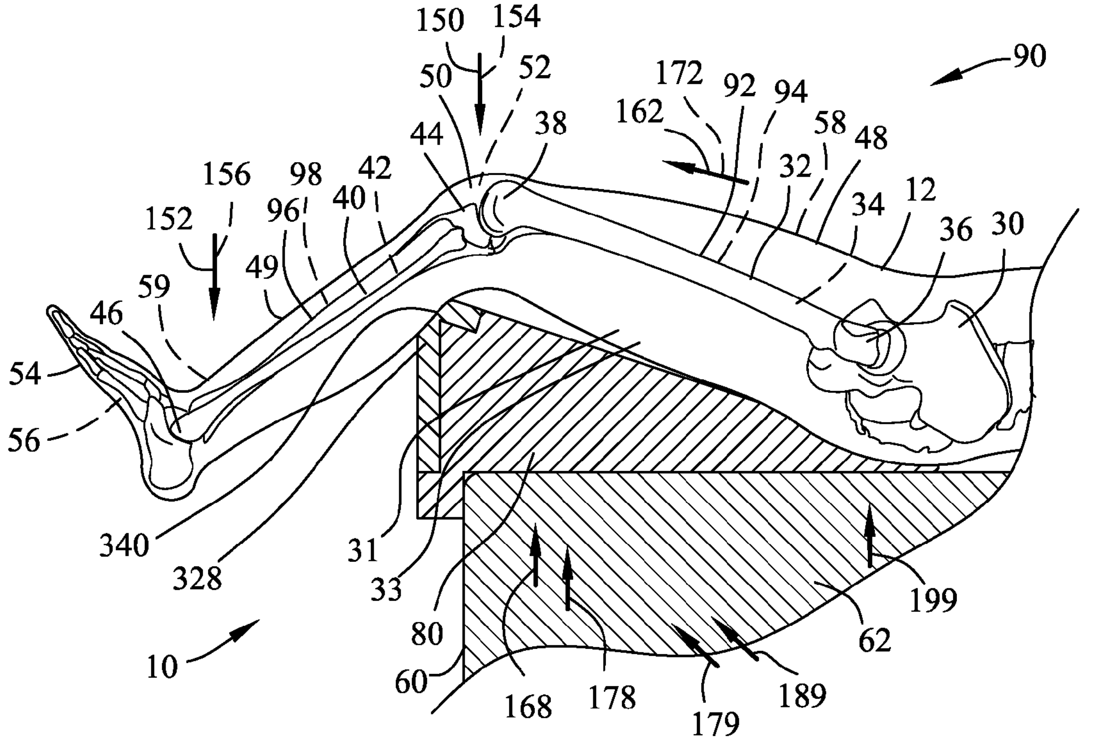
FIG. 28 is a sectional view along line 28-28 in FIG. 26 illustrating the supplemental support layer permitting an increased displacement for increasing the surface area between the first femur and the second femur for increasing comfort and preventing body circulation problems.
Figure 29:
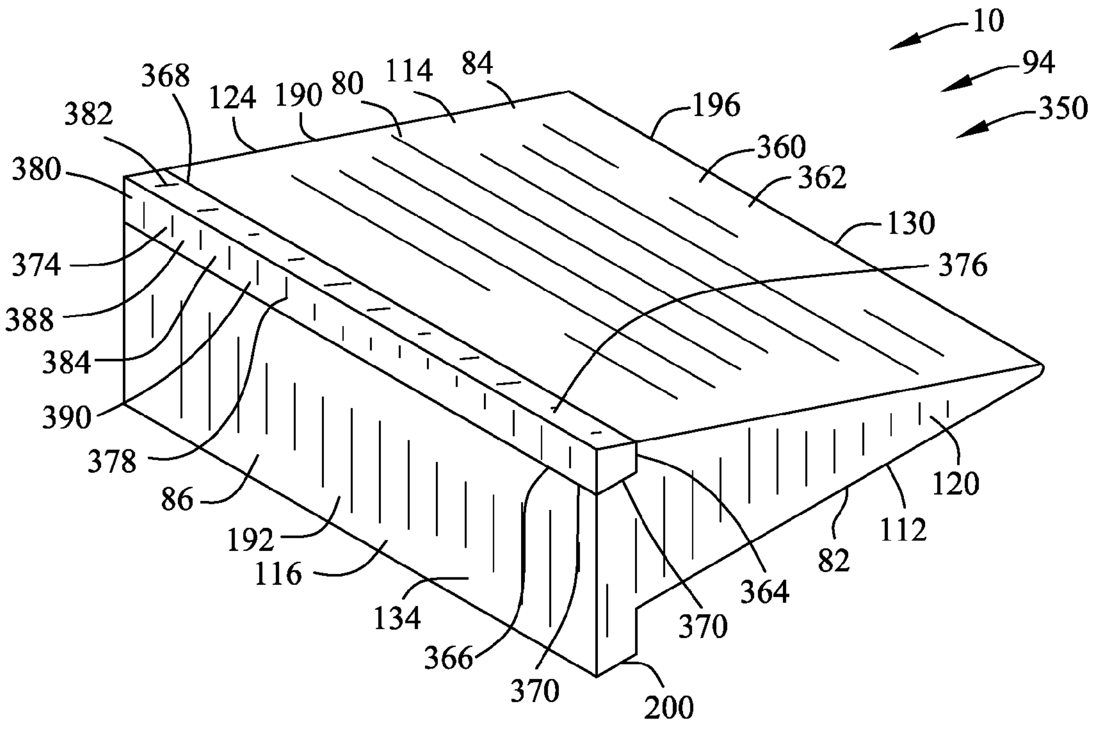
FIG. 29 is a top isometric view of a fifth embodiment of the vertebral column traction device for expanding the vertebral column of an individual wherein the pivot area includes a supplemental support layer positioned within a groove.
Figure 30:
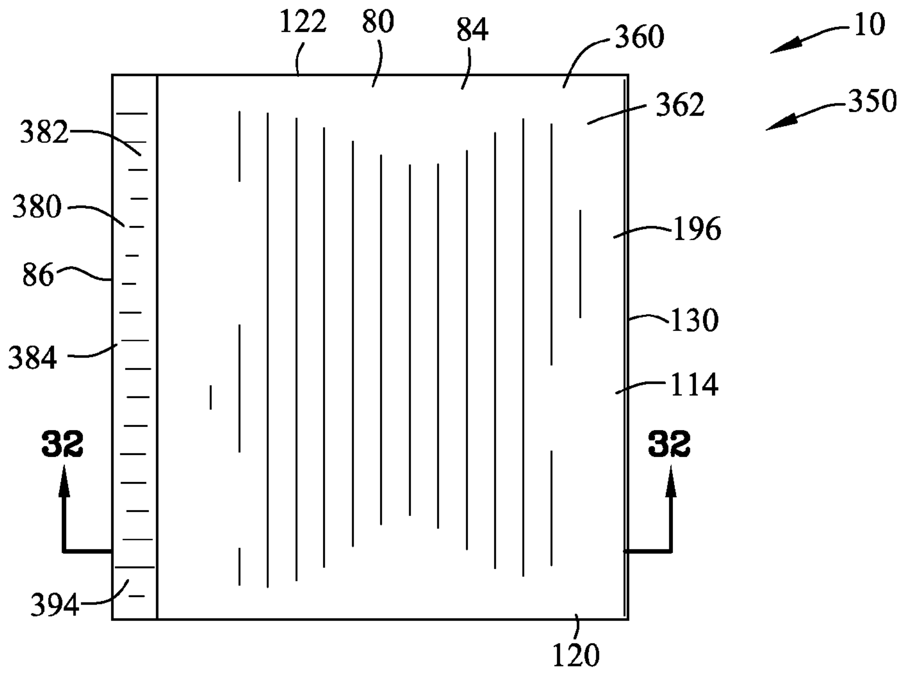
FIG. 30 is a top view of FIG. 29.
Figure 31:
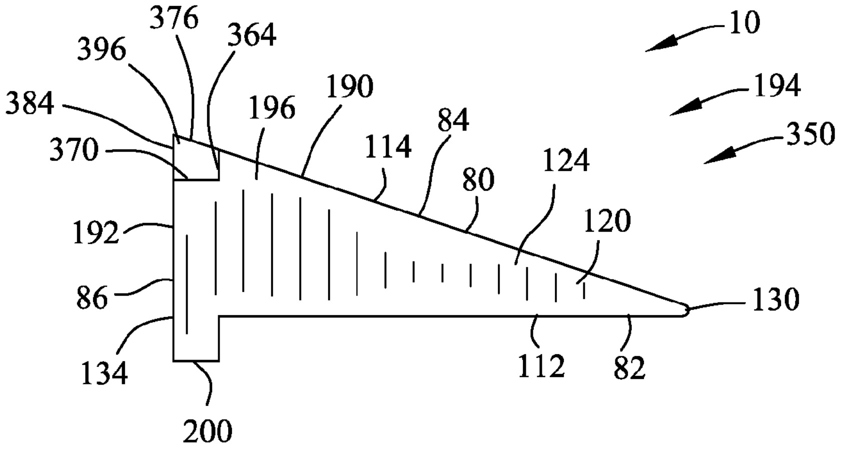
FIG. 31 is a side view of FIG. 29.
Figure 32:
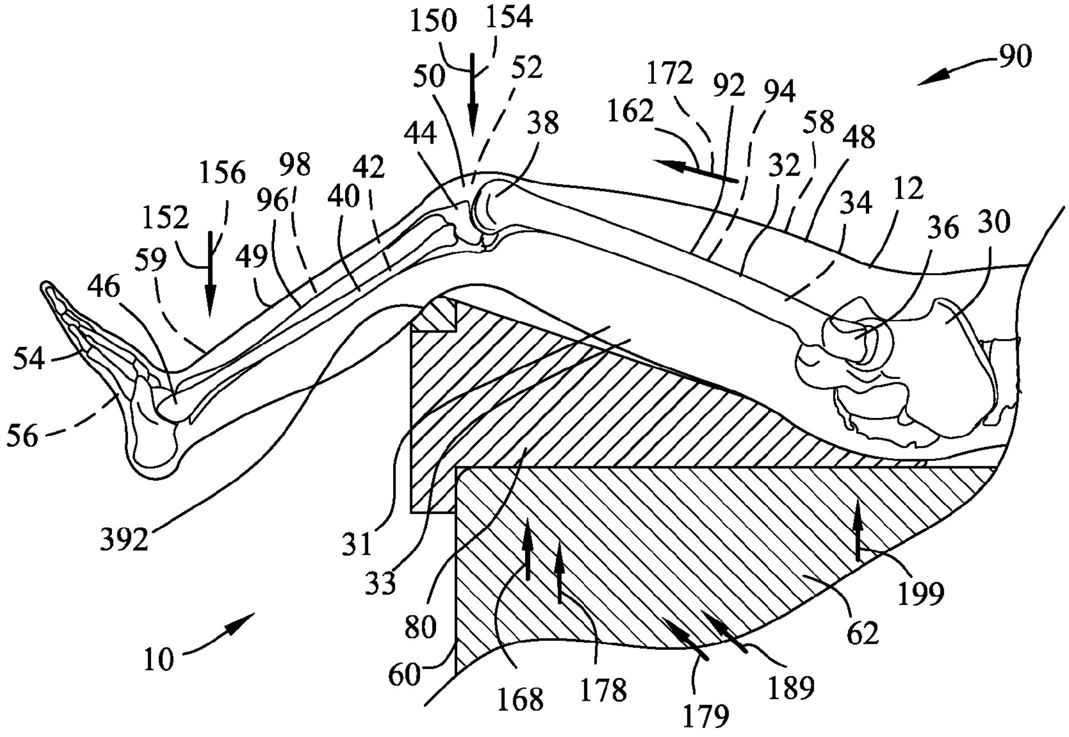
FIG. 32 is a sectional view along line 32-32 in FIG. 30 illustrating the supplemental support layer permitting an increased displacement for increasing the surface area between the first femur and the second femur for increasing comfort and preventing body circulation problems.
Figure 33:
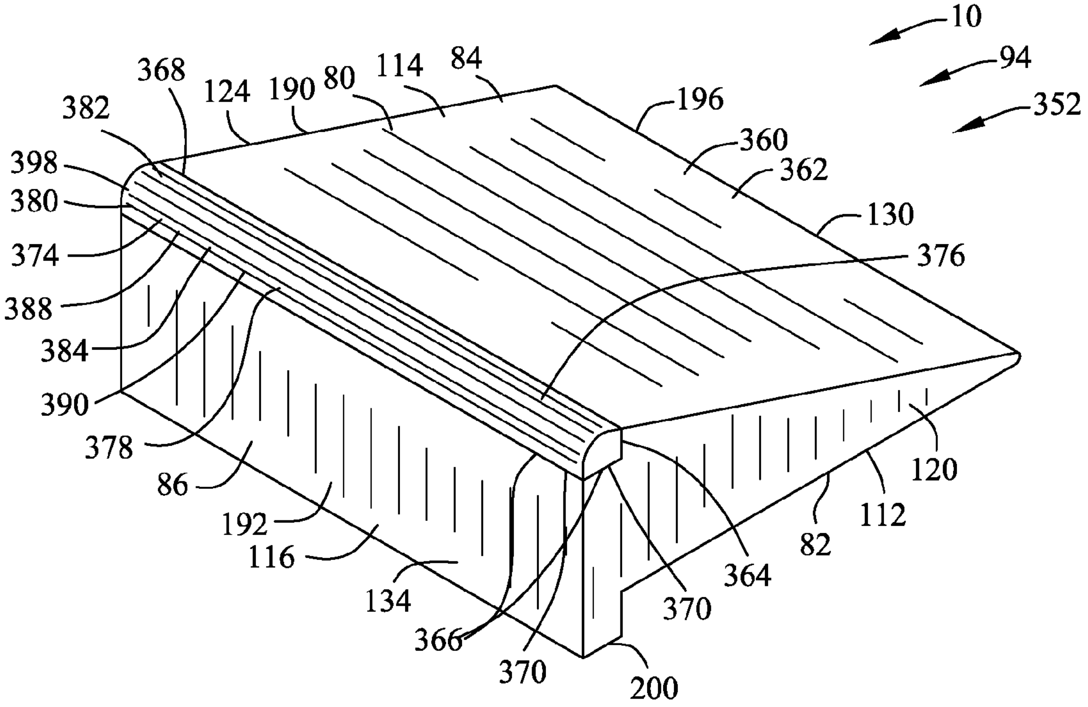
FIG. 33 is a top isometric view of a sixth embodiment of the vertebral column traction device for expanding the vertebral column of an individual wherein the pivot area includes a supplemental support layer positioned within a groove.
Figure 34:
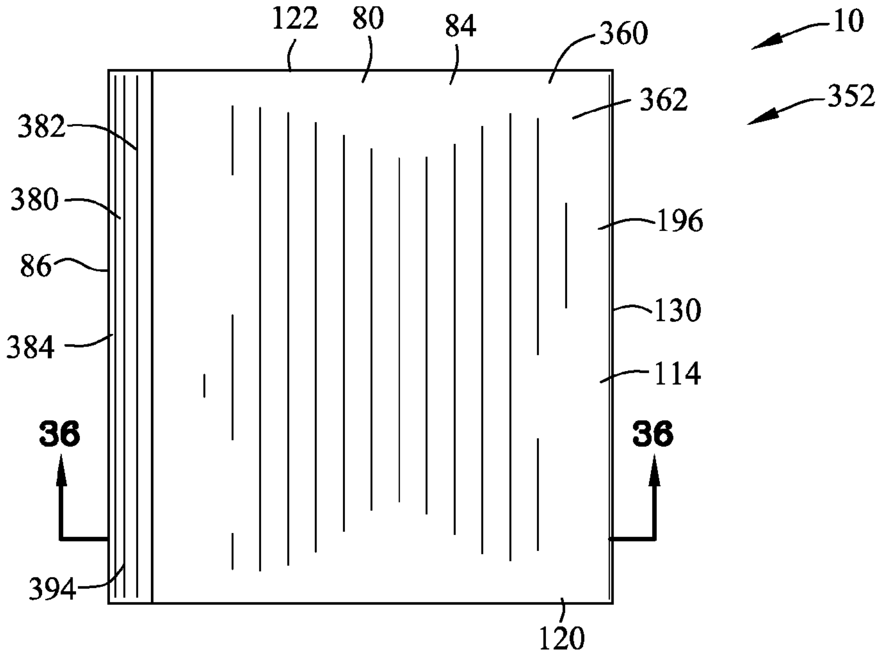
FIG. 34 is a top view of FIG. 33.
Figure 35:
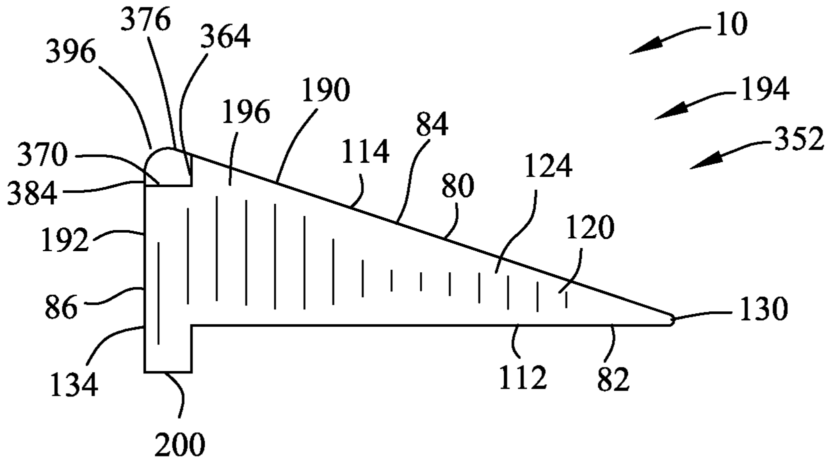
FIG. 35 is a side view of FIG. 33.
Figure 36:
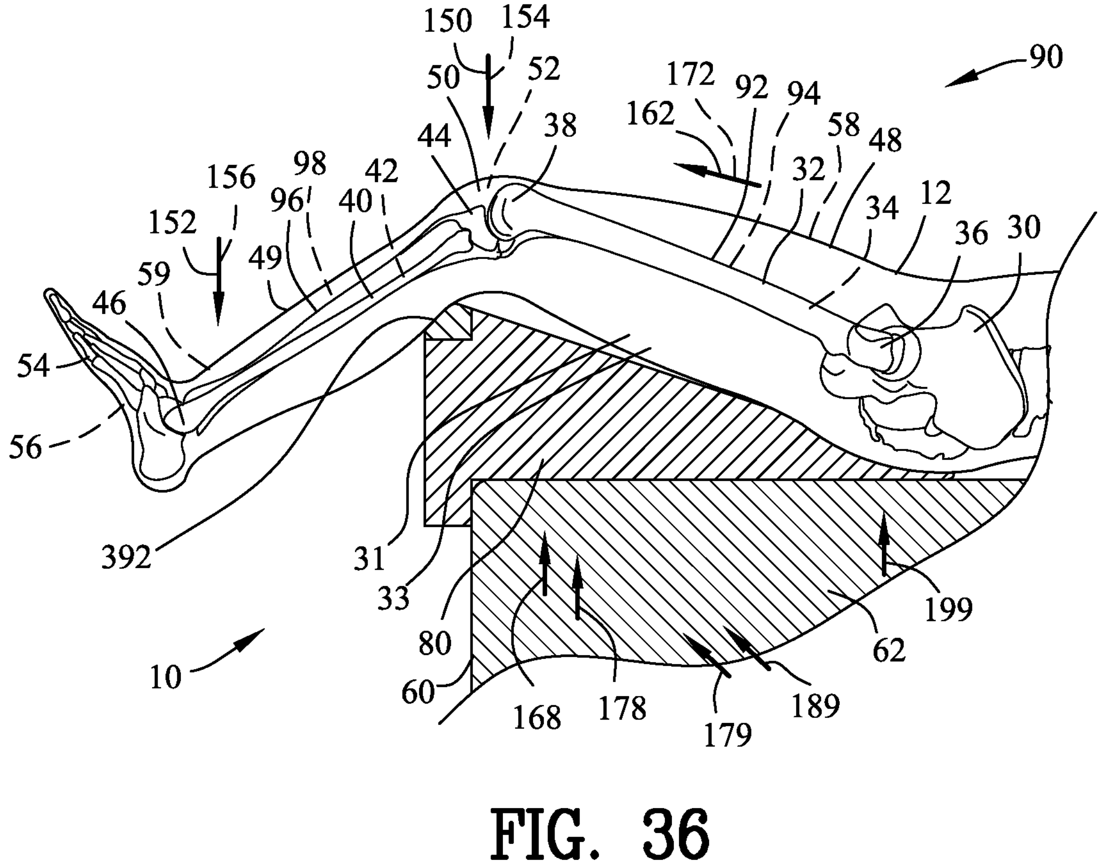
FIG. 36 is a sectional view along line 36-36 in FIG. 34 illustrating the supplemental support layer permitting an increased displacement for increasing the surface area between the first femur and the second femur for increasing comfort and preventing body circulation problems.
Figure 37:
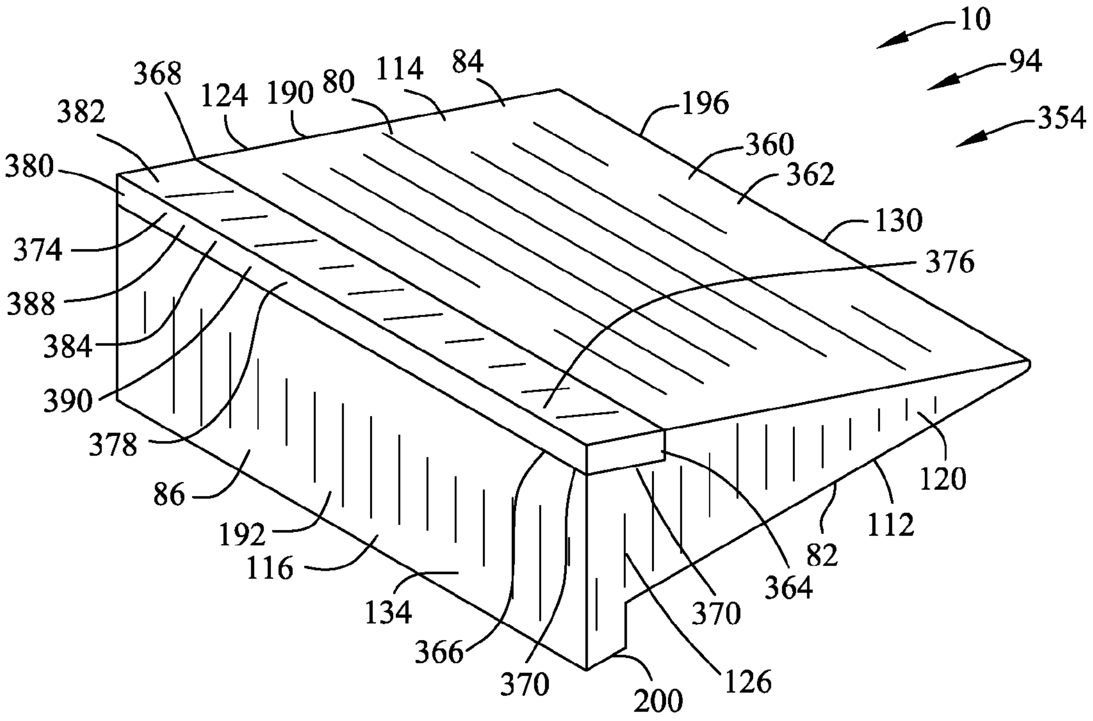
FIG. 37 is a top isometric view of a seventh embodiment of the vertebral column traction device for expanding the vertebral column of an individual wherein the pivot area includes a supplemental support layer positioned within a groove.
Figure 38:
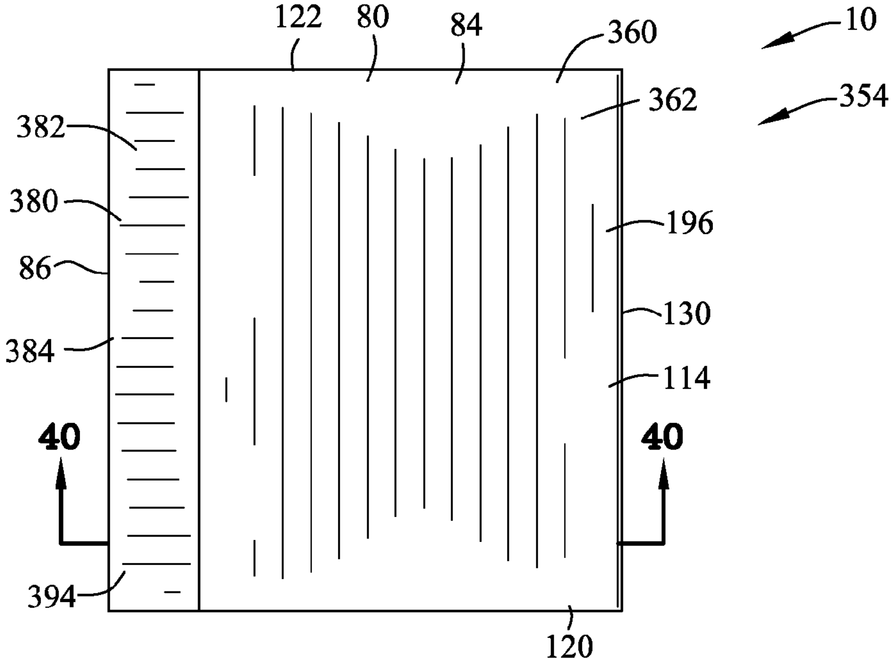
FIG. 38 is a top view of FIG. 37.
Figure 39:
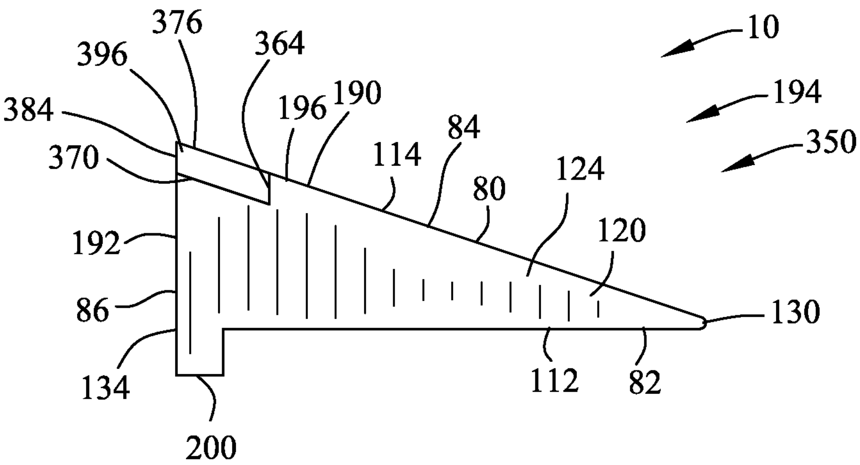
FIG. 39 is a side view of FIG. 37.
Figure 40:
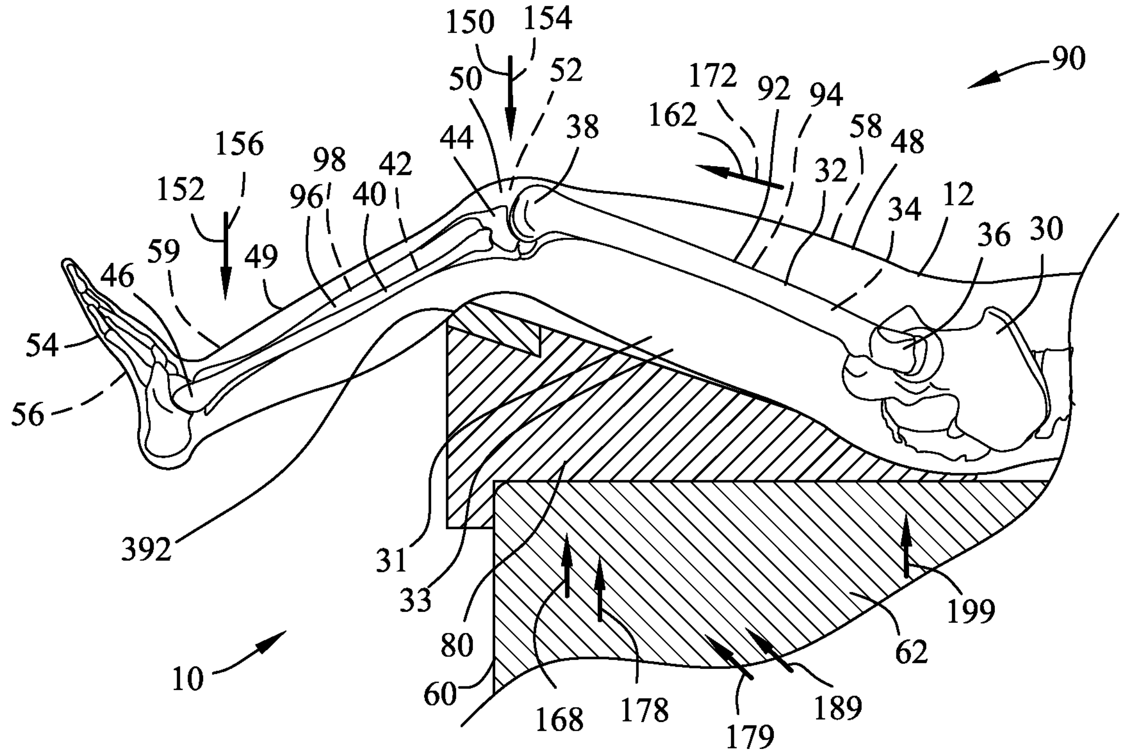
FIG. 40 is a sectional view along line 40-40 in FIG. 38 illustrating the supplemental support layer permitting an increased displacement for increasing the surface area between the first femur and the second femur for increasing comfort and preventing body circulation problems.
Figure 41:
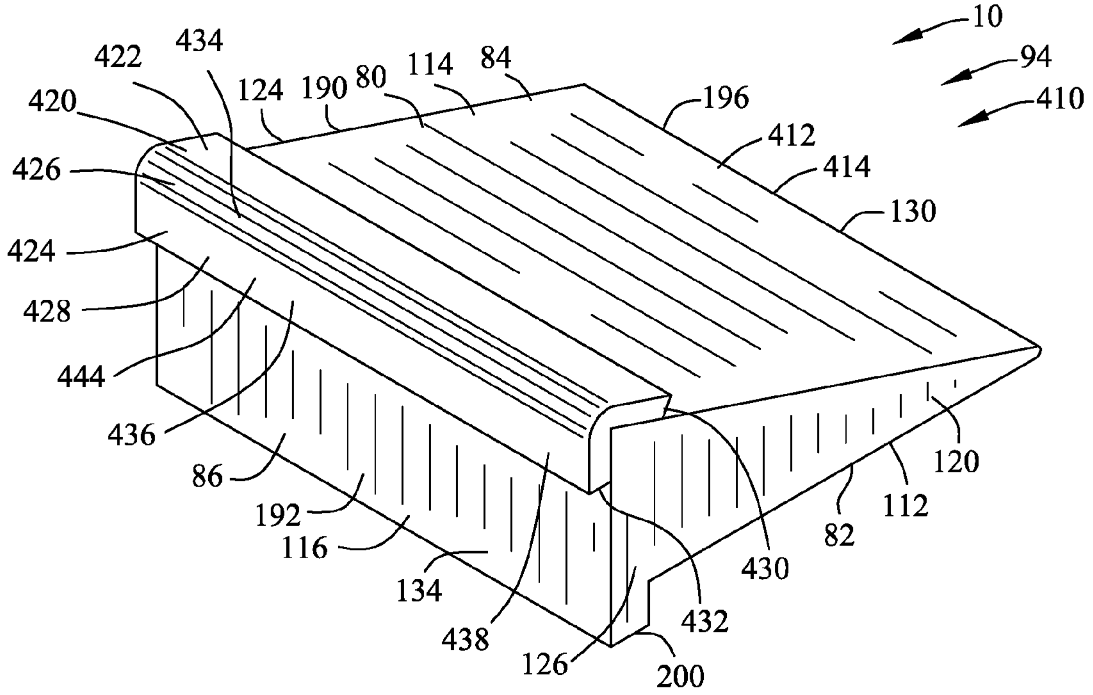
FIG. 41 is a top isometric view of a eighth embodiment of the vertebral column traction device for expanding the vertebral column of an individual wherein the pivot area includes a supplemental support layer positioned within a groove.
Figure 42:
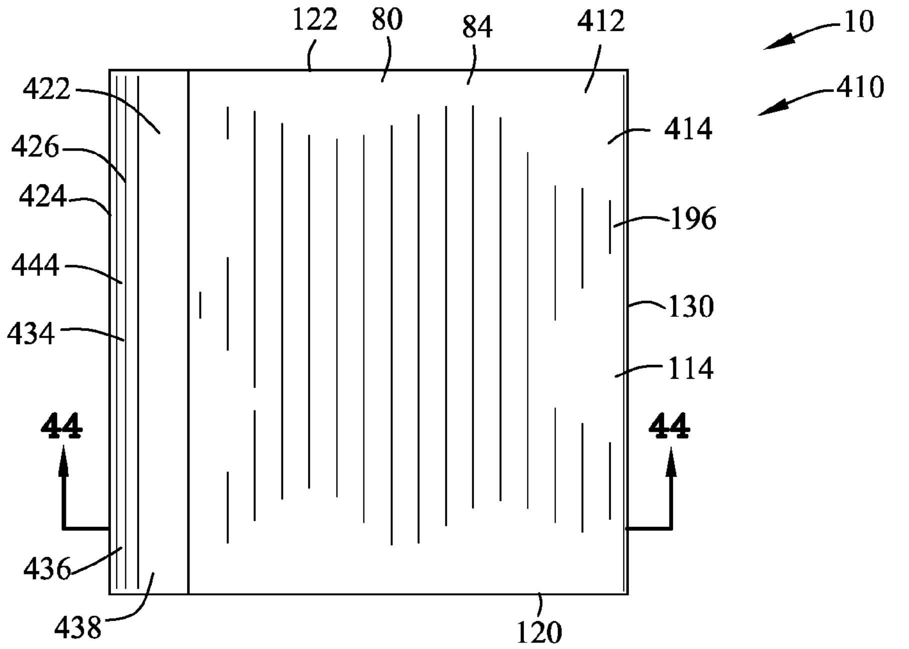
FIG. 42 is a top view of FIG. 41.
Figure 43:
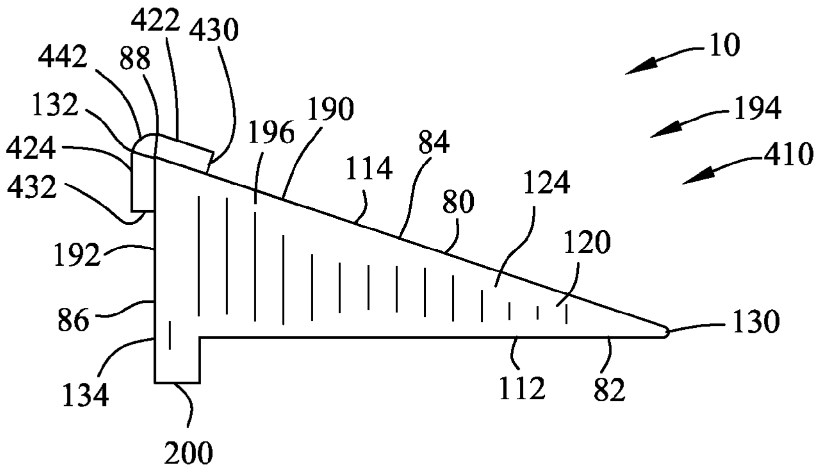
FIG. 43 is a side view of FIG. 41.
Figure 44:
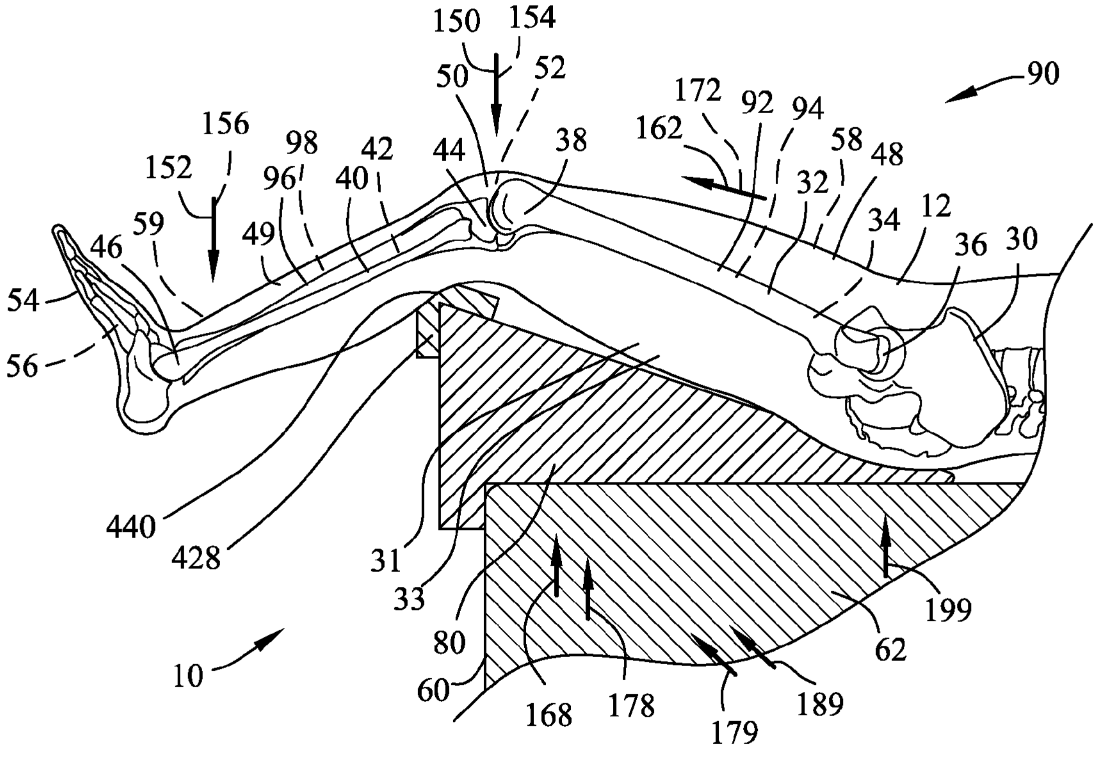
FIG. 44 is a sectional view along line 44-44 in FIG. 42 illustrating the supplemental support layer permitting an increased displacement for increasing the surface area between the first femur and the second femur for increasing comfort and preventing body circulation problems.
Figure 45:
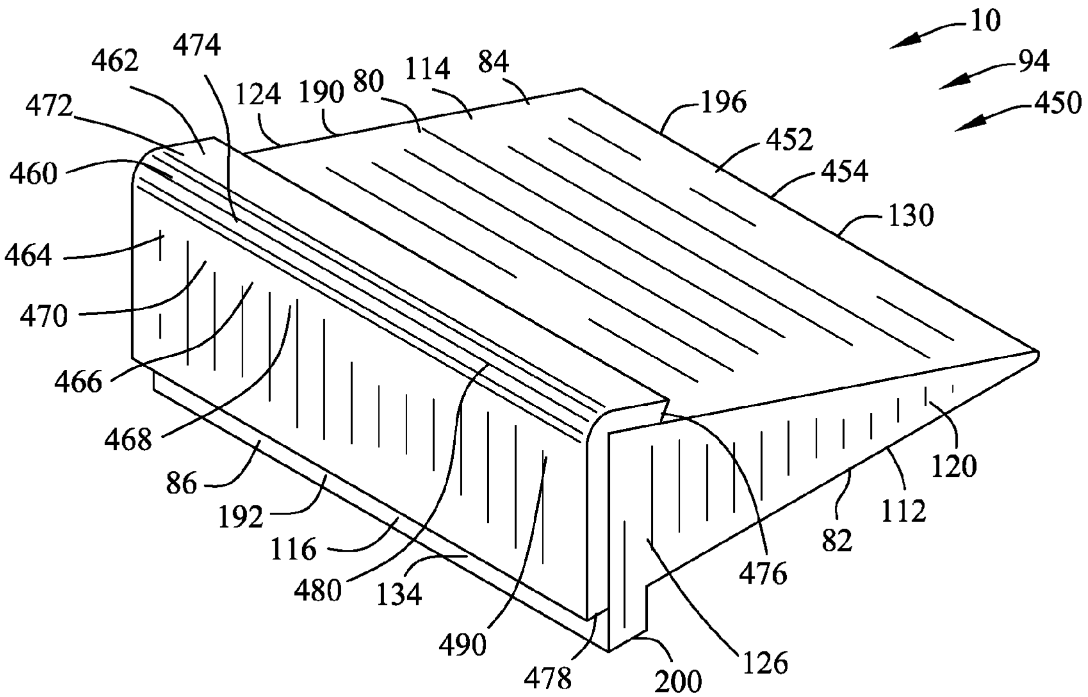
FIG. 45 is a top isometric view of a ninth embodiment of the vertebral column traction device for expanding the vertebral column of an individual wherein the pivot area includes a supplemental support layer positioned within a groove.
Figure 46:
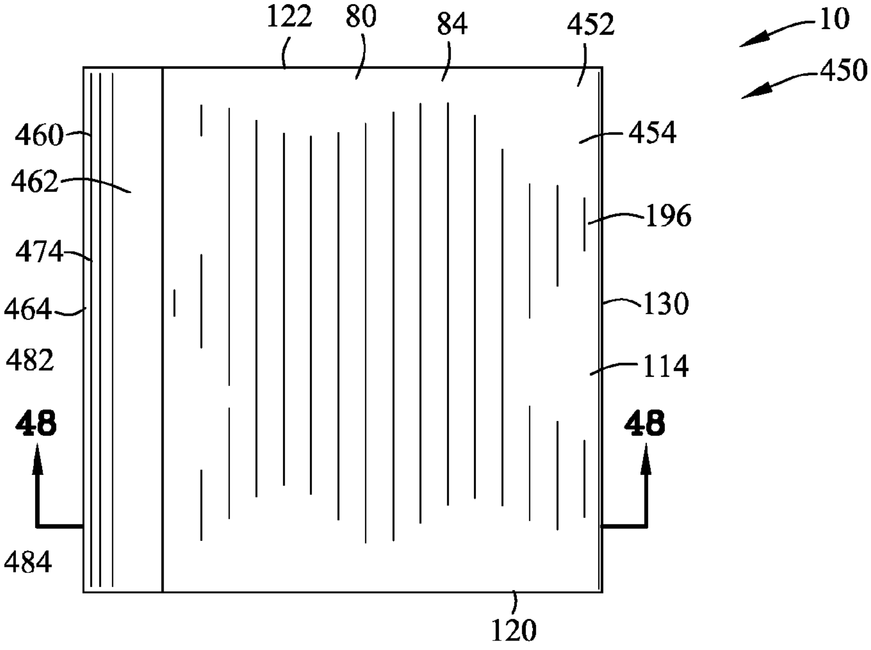
FIG. 46 is a top view of FIG. 45.
Figure 47:
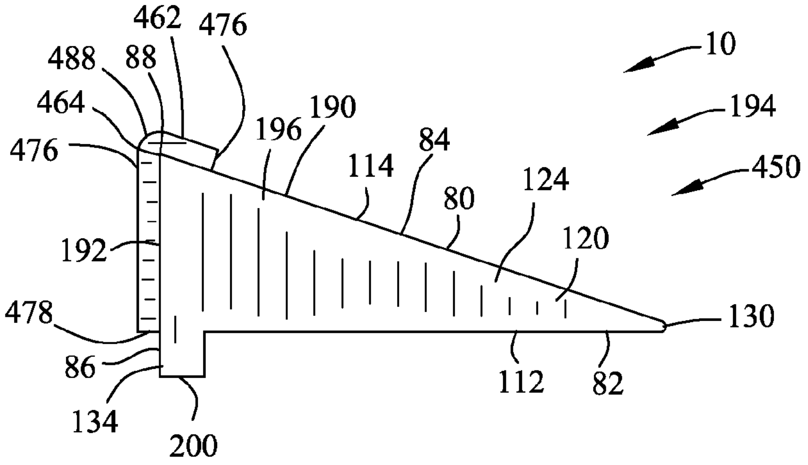
FIG. 47 is a side view of FIG. 45.
Figure 48:
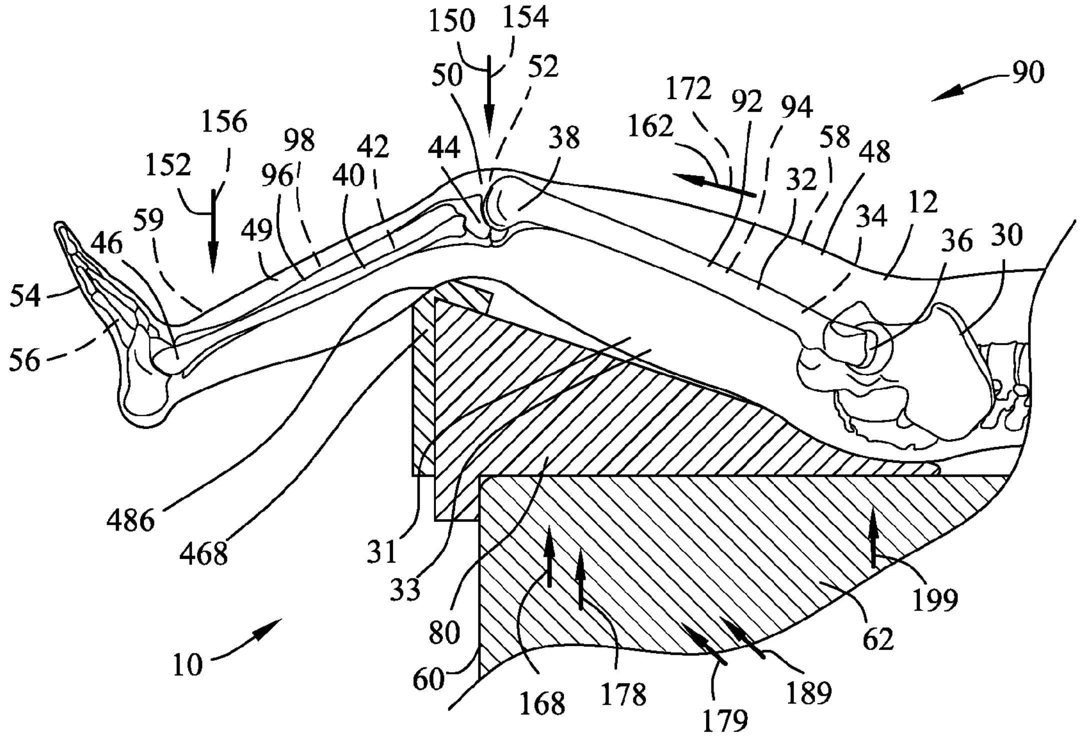
FIG. 48 is a sectional view along line 48-48 in FIG. 46 illustrating the supplemental support layer permitting an increased displacement for increasing the surface area between the first femur and the second femur for increasing comfort and preventing body circulation problems.
Figure 49:
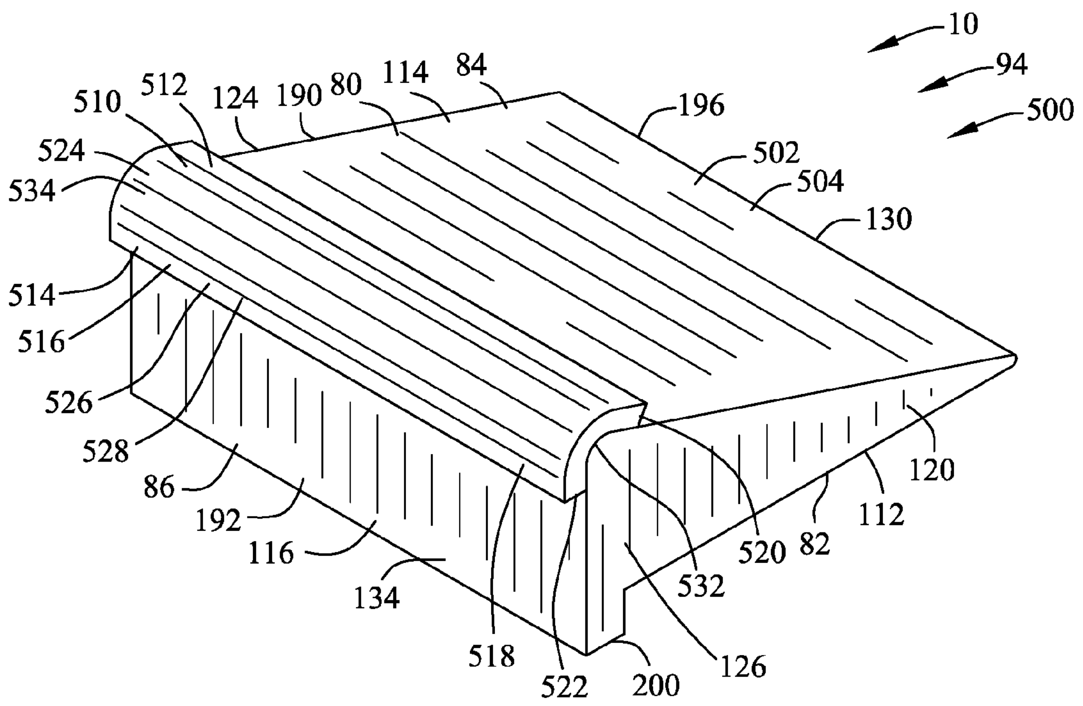
FIG. 49 is a top isometric view of a tenth embodiment of the vertebral column traction device for expanding the vertebral column of an individual wherein the pivot area includes a supplemental support layer positioned within a groove.
Figure 50:
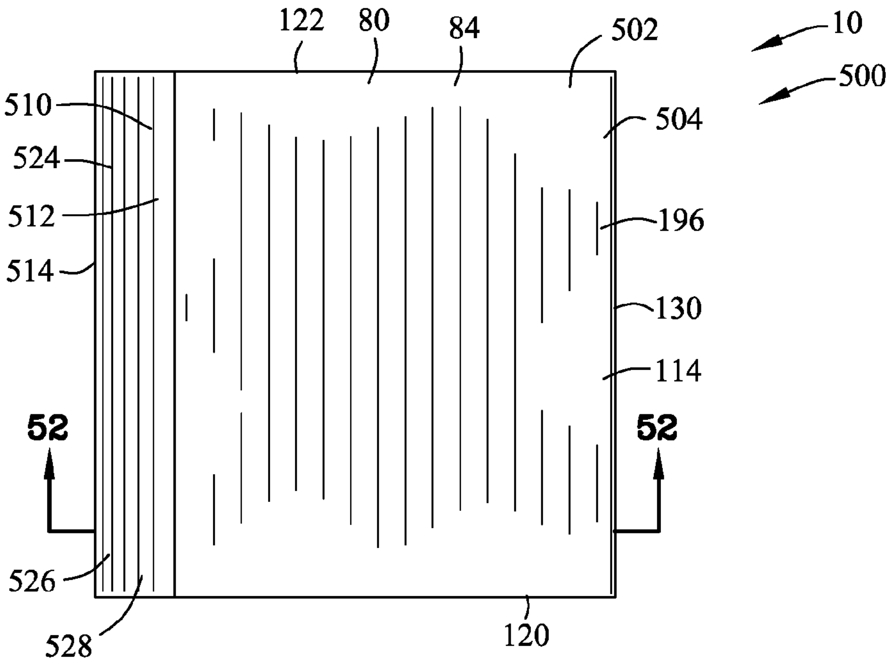
FIG. 50 is a top view of FIG. 49.
Figure 51:
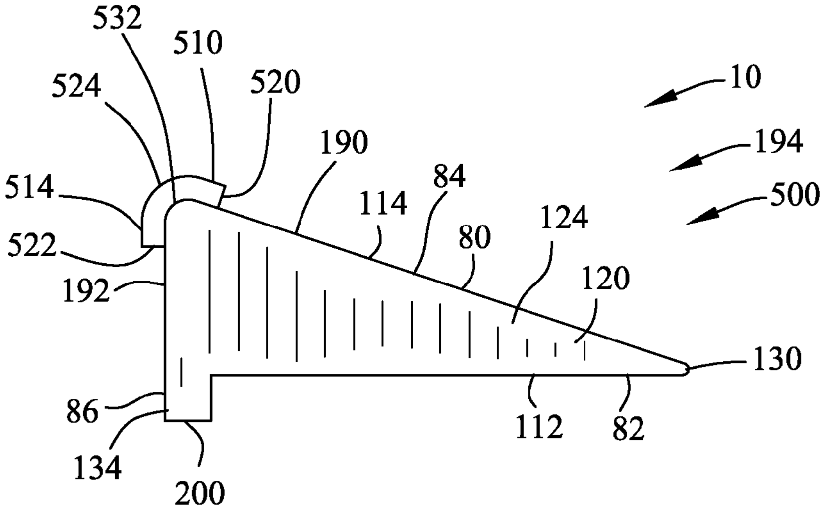
FIG. 51 is a side view of FIG. 49.
Figure 52:
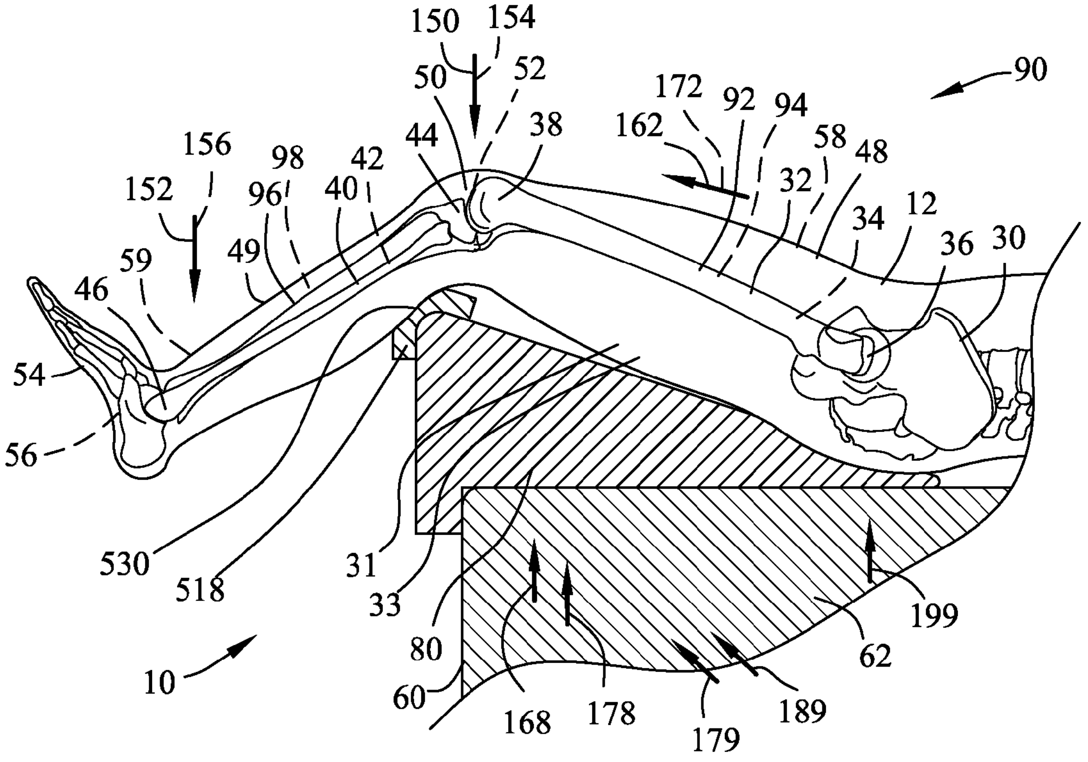
FIG. 52 is a sectional view along line 52-52 in FIG. 50 illustrating the supplemental support layer permitting an increased displacement for increasing the surface area between the first femur and the second femur for increasing comfort and preventing body circulation problems.
Figure 53:
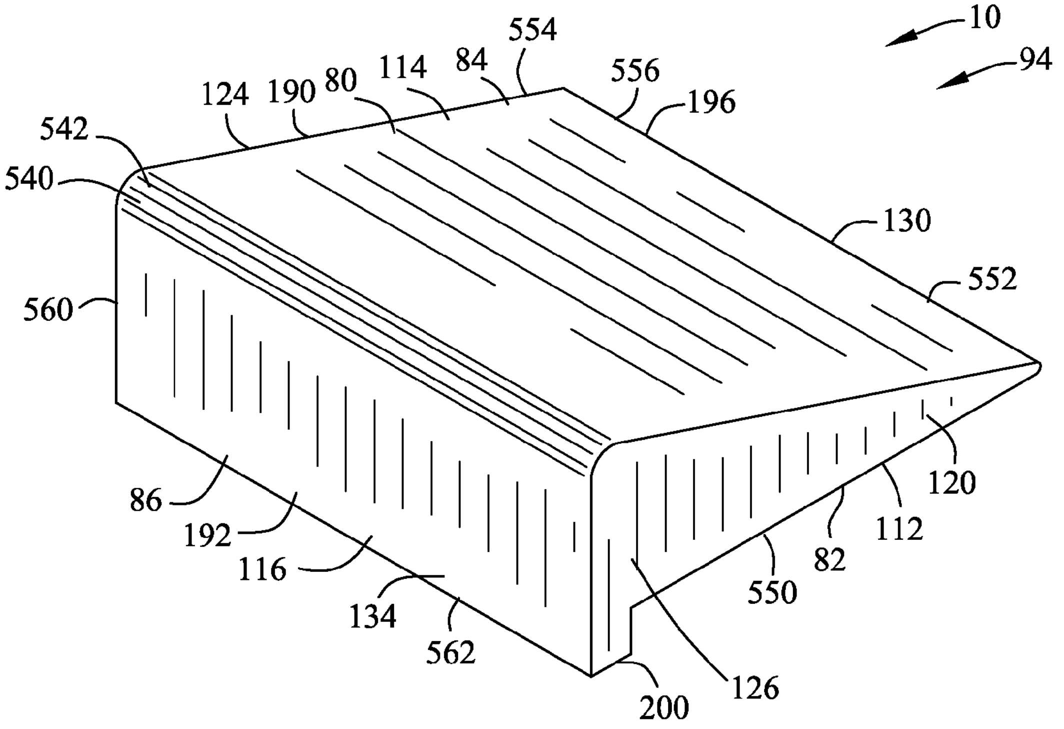
FIG. 53 is a top isometric view of a eleventh embodiment of the vertebral column traction device for expanding the vertebral column of an individual wherein the pivot area includes a curve radius.
Figure 54:
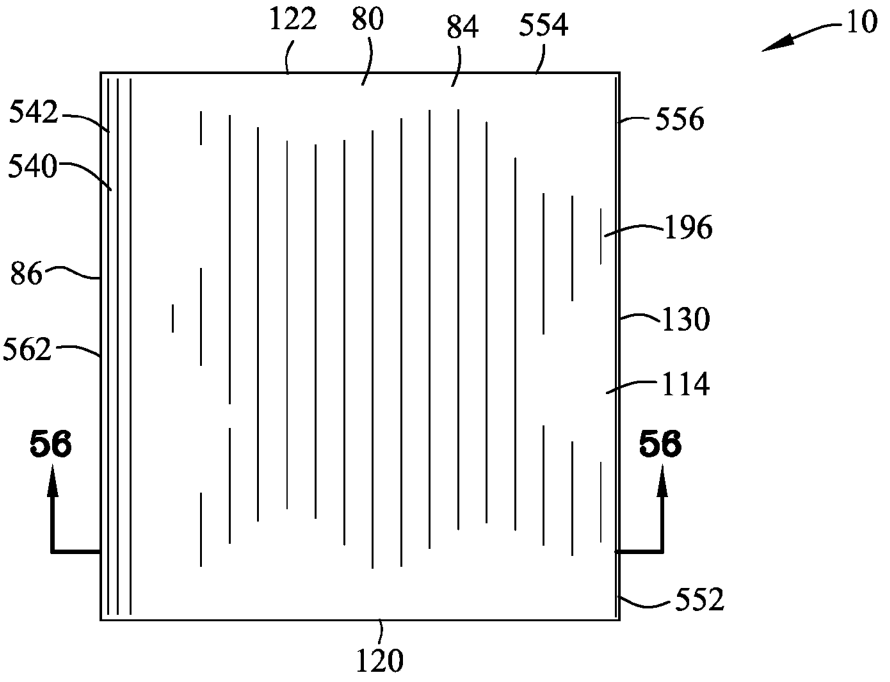
FIG. 54 is a top view of FIG. 53.
Figure 55:
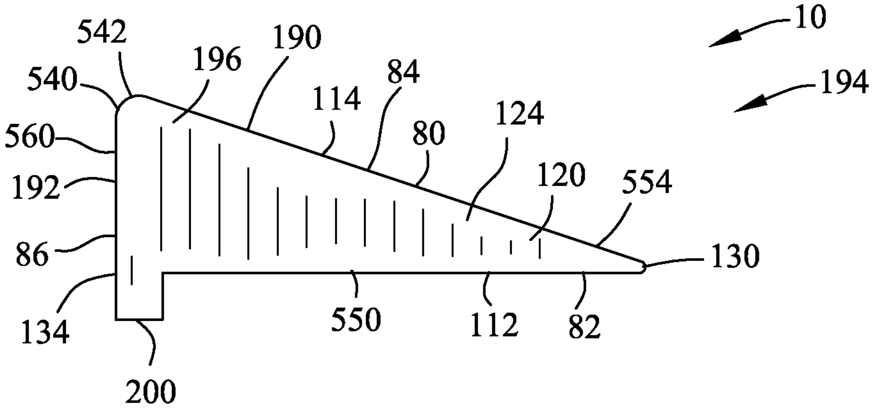
FIG. 55 is a side view of FIG. 53.
Figure 56:
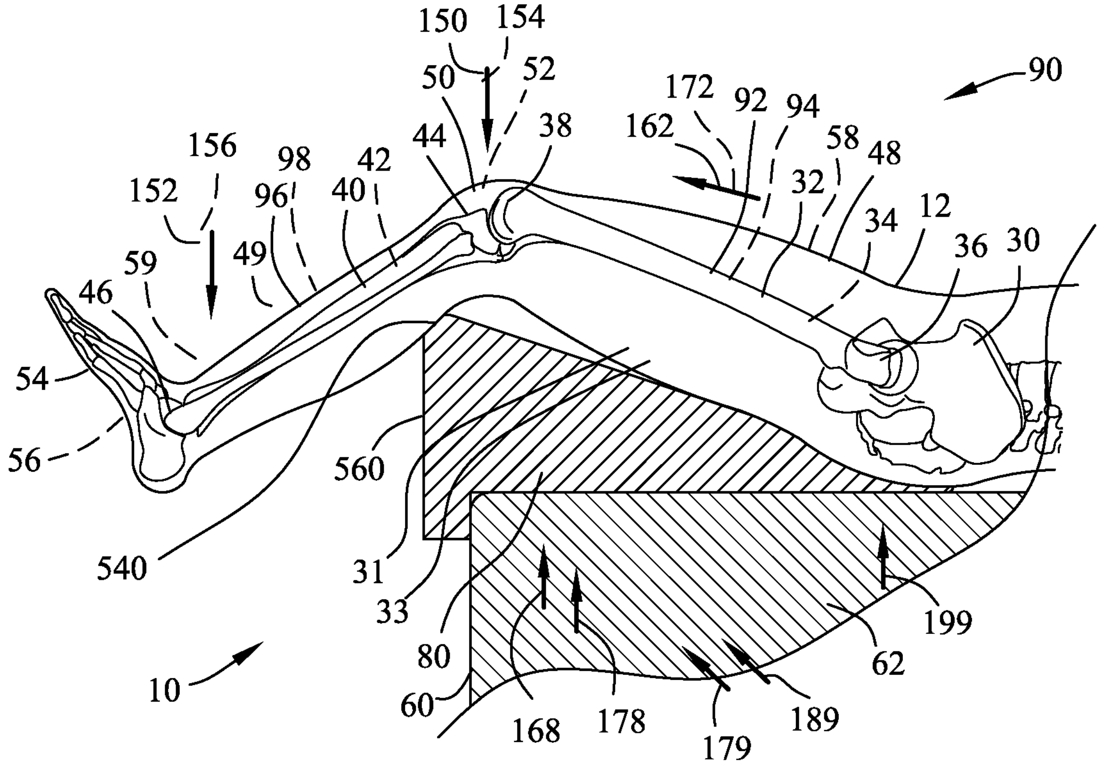
FIG. 56 is a sectional view along line 56-56 in FIG. 54 illustrating the curve radius permitting an increased displacement for increasing the surface area between the first femur and the second femur for increasing comfort and preventing body circulation problems.
Figure 58:
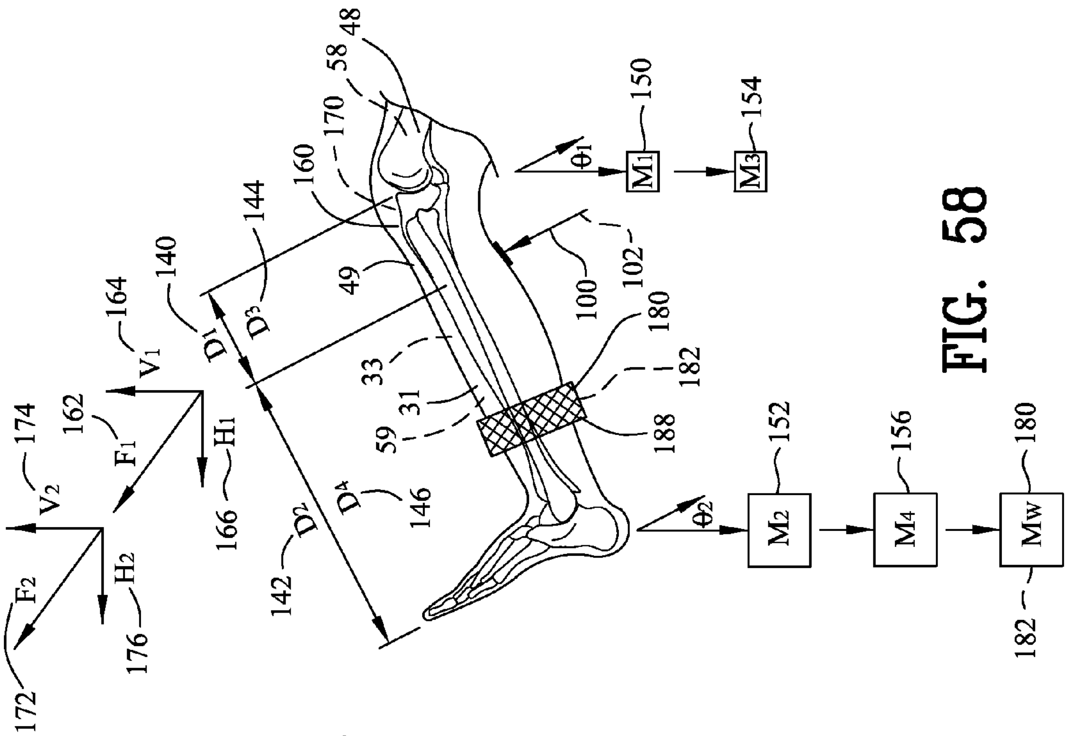
FIG. 58 is a view similar to FIG. 20 illustrating the first lever, the second lever and the annular weight belt in conjunction with an increased contact surface area between the vertebral column traction device and the first femur and the second femur for increasing comfort and preventing body circulation problems.
Figure 57:
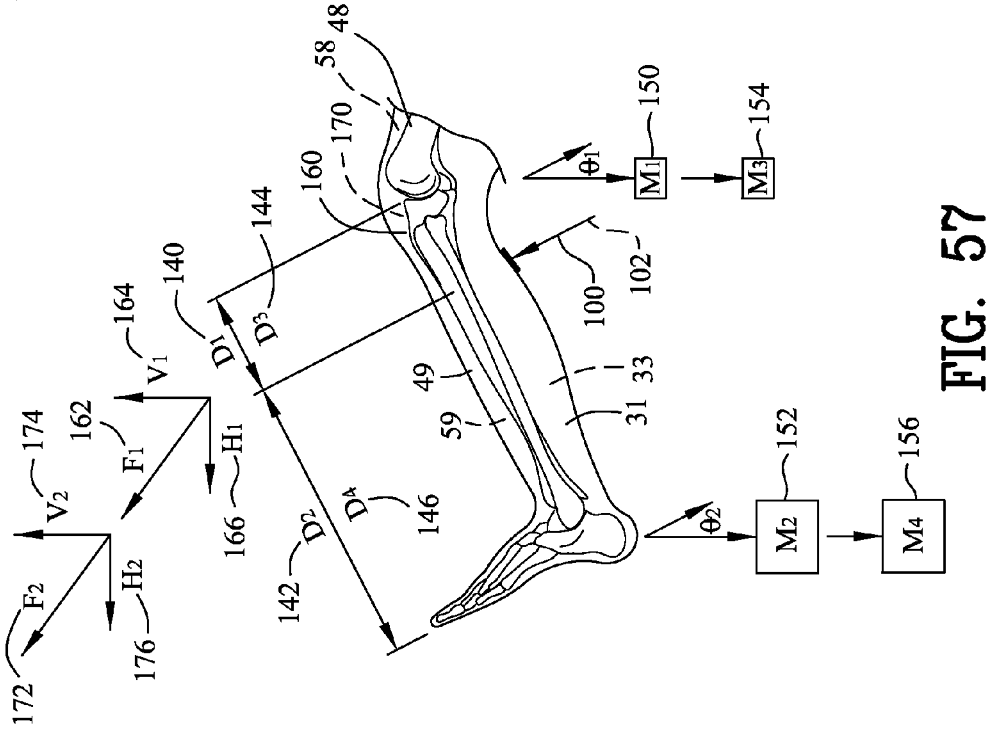
FIG. 57 is a view similar to FIG. 19 illustrating the first lever and the second lever in conjunction with an increased contact surface area between the vertebral column traction device and the first femur and the second femur for increasing comfort and preventing body circulation problems.

The fourth mass 156 is greater than the third mass 154 for creating a secondary mechanical advantage output force 172 from the second lever 170 including a second ascending vertical force 174 and a second distal horizontal force 176 in the third distance 144. The secondary mechanical advantage output force 172 is conveyed from the second femur 34, through the pelvis 30 and to the vertebral column 20 for expanding the vertebral column 20 of an individual 12. As illustrated in FIG. 19, the below equation may be utilized for computing the primary mechanical advantage output force 162 and the secondary mechanical advantage output force 172 respectively:

$$D2\ M2 \cos 2\ \theta2 = D1\ M1 \cos 1\ \theta1$$

$$D4\ M4 \cos 2\ \theta2 = D3 M3 \cos 1\ \theta1$$

The primary mechanical advantage output force 162 and the secondary mechanical advantage output force 172 expose the vertebral column 20 to a compound force for expanding the vertebral column 20. The expansion of the vertebral column 20 may promote hydration of the plurality of intervertebral discs 28 and potentially avoid spinal stenosis. More specifically, the expansion of the plurality of intervertebral discs 28 may prompt bodily fluids back into the plurality of intervertebral discs 28 and thus alleviate spinal stenosis. The vertebral column traction device 10 is intended to be utilized for a portion of the day in order to expand the vertebral column and promoting rehydration of the plurality of intervertebral discs 28 and thus alleviate spinal stenosis and other spinal ailments.

Figure 17:
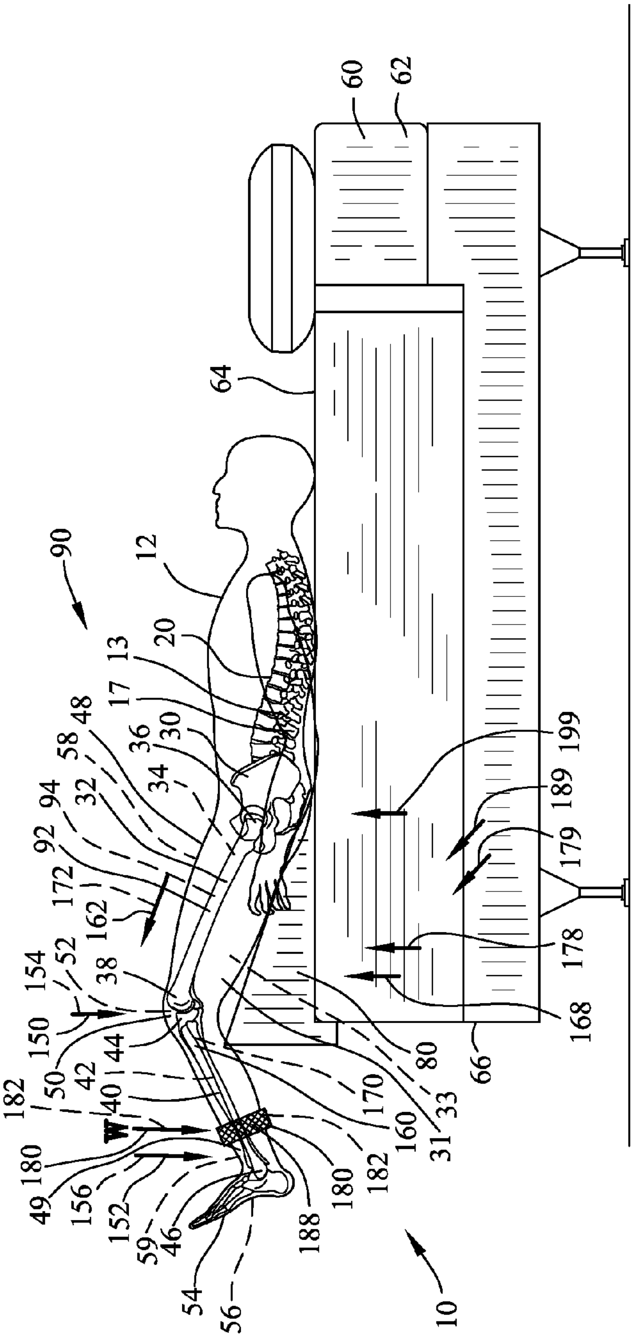
FIG. 17 is a view similar to FIG. 11 illustrating a first supplementary weight and a second supplementary weight coupled to a first tibia and a second tibia respectively.
Figure 18:
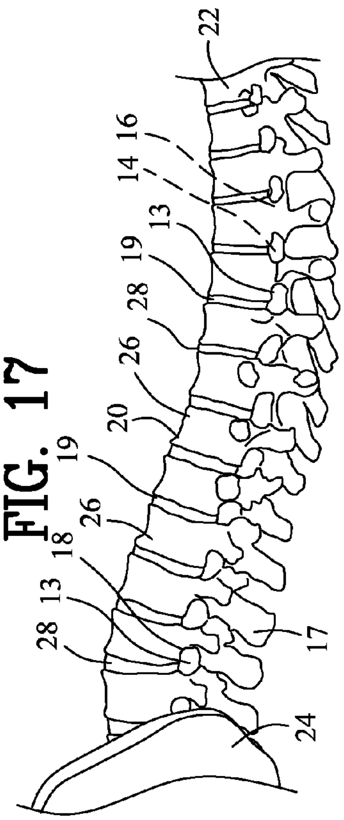
FIG. 18 is an enlarge view of a portion of FIG. 17 illustrating an expanded vertebral column.
Figure 20:
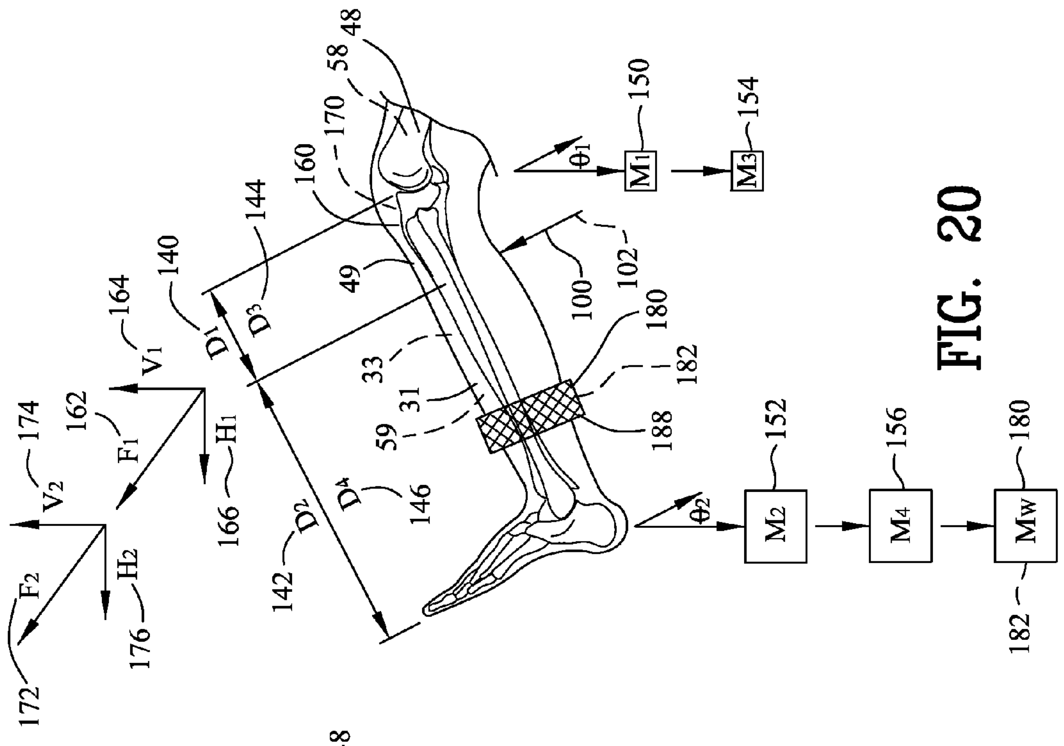
FIG. 20 is an enlarged view of a portion of FIG. 17 illustrating a first lever and a second lever.

As shown in FIGS. 17, 18 and 20, a first supplementary weight 180 is coupled to the first tibia 40 or the first foot 54 for increasing the second mass 152 and increasing the primary mechanical advantage output force 162 to further expand the vertebral column 20 of the individual 12. A second supplementary weight 182 is coupled to the second tibia 42 or the second foot 56 for increasing the fourth mass 156 and increasing the secondary mechanical advantage output force 172 to further expand the vertebral column 20 of the individual 12. The first supplementary weight 180 and the second supplementary weight 182 may include an annular weight belt 188, a bar belt with strap or other weight. The below equation may be utilized for computing the increased primary mechanical advantage output force 184 and the increased secondary mechanical advantage output force 186 respectively:

$$D2(M2+MW)\cos 2\ \theta2 = D1\ M1 \cos 1\ \theta1$$

$$D4(M4+MW)\cos 2\ \theta2 = D3M3 \cos 1\ \theta1$$

The increased primary mechanical advantage output force 184 and the increased secondary mechanical advantage output force 186 expose the vertebral column 20 to a compound force for expanding the vertebral column 20. The expansion of the vertebral column 20 may promote hydration of the plurality of intervertebral discs 28 and potentially avoid spinal stenosis. More specifically, the expansion of the plurality of intervertebral discs 28 may prompt bodily fluids back into the plurality of intervertebral discs 28 and thus alleviate spinal stenosis. The vertebral column traction device 10 is intended to be utilized for a portion of the day in order to expand the vertebral column and promoting rehydration of the plurality of intervertebral discs 28 and thus alleviate spinal stenosis and other spinal ailments.

In a more specific embodiment of the invention, the first triangle plane surface 120 and the second triangle plane surface 122 of the support body 80 include a right triangle 126. The inclined plane surface 114 includes an inclined length 190. The riser plane surface 116 includes a riser length 192. The base plane surface 112 includes a base length 193. The inclined length 190 and the riser length 192 may define a three to one length ratio 194 respectively.

The support body 80 may be construction of a closed-cell foam 196, an open-cell foam 196 or other rigid or semi-rigid materials. More specifically, the support body 80 may be comprised of natural latex foam rubber or polyurethane foam commonly referred to as memory foam either in their unadulterated forms or mixed with other chemicals as open-cell or closed-cell material. Preferably, the construction of the support body 80 is a foam 196 which quickly molds to the shape of the individual 12 and thereafter quickly returns to its original shape once the individual 12 is removed from the support body 80. The foam 196 may have a mixture that is calibrated to achieve the maximum or optimum resilience so that the compression of the support body 80 at the pivot area 88 and at the front surface 84 will result in continuing positive outward pressure against the first lower limb 49 and the second lower limb 59 at the compressed pivot area 88 and the first upper limb 48 and the second upper limb 58 at the compressed front surface 84 of the support body 80. The continuing positive outward pressure increases the primary mechanical advantage output force 162 and the secondary mechanical output force 172 as the resilient pivot area 88 and the front surface 84 of the support body 80 tend to return to their original shapes and positions.

In other words, the foam 196 provides a spring back force. The front surface 84 provides a first foam force 168 and a second foam force 178 upon the first upper limb 48 and the second upper limb 58 respectively. The pivot area 88 provides a third foam force 179 and a fourth foam force 189 upon the first lower limb 49 and the second lower limb 59 respectively. The front surface 84 further provides a fifth foam force 199 upon the pelvis 30. The first foam force 168 and the second foam force 178 are conveyed from the first femur 32 and the second femur 34, through the pelvis 30 and to the vertebral column 20 for expanding the vertebral column 20 of an individual 12. The third foam force 179 and the fourth foam force 189 are conveyed from the first tibia 40 and the second tibia 42, through the first knee joint 50 and the second knee joint 52, through the first femur 32 and the second femur 34, through the pelvis 30 and to the vertebral column 20 for expanding the vertebral column 20 of an individual 12. The fifth foam force 199 is conveyed from the pelvis 30 and to the vertebral column 20 for expanding the vertebral column 20 of an individual 12.

Figure 13:
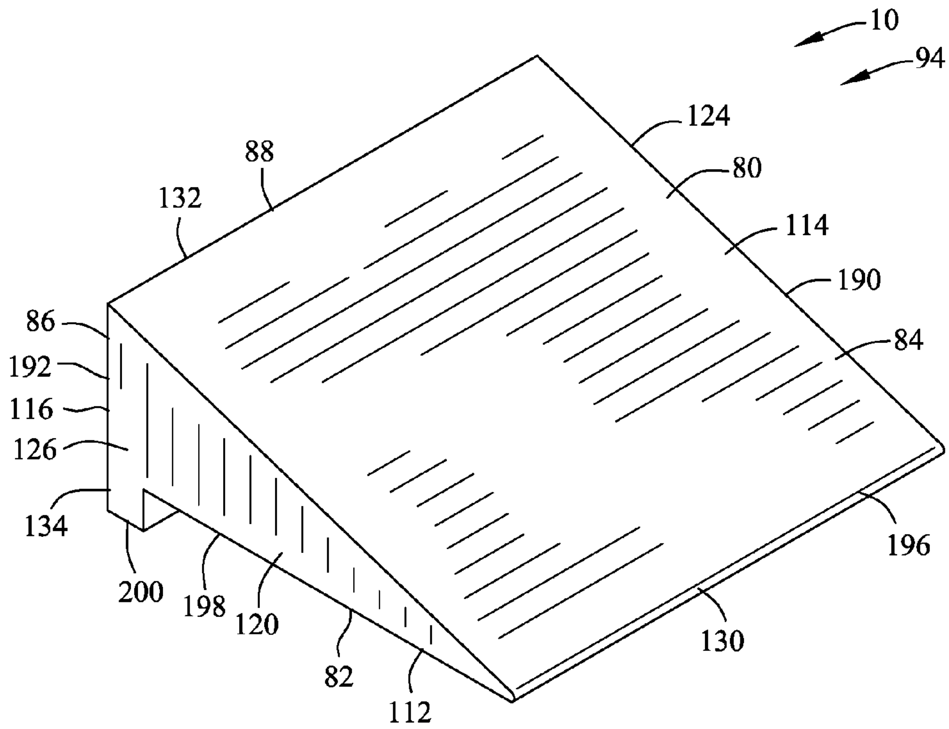
FIG. 13 is a top isometric view of a second embodiment of a vertebral column traction device for expanding the vertebral column of an individual wherein the a polymeric layer is coupled to a base plane surface for increasing the coefficient of friction between the support body and the support surface.
Figure 14:
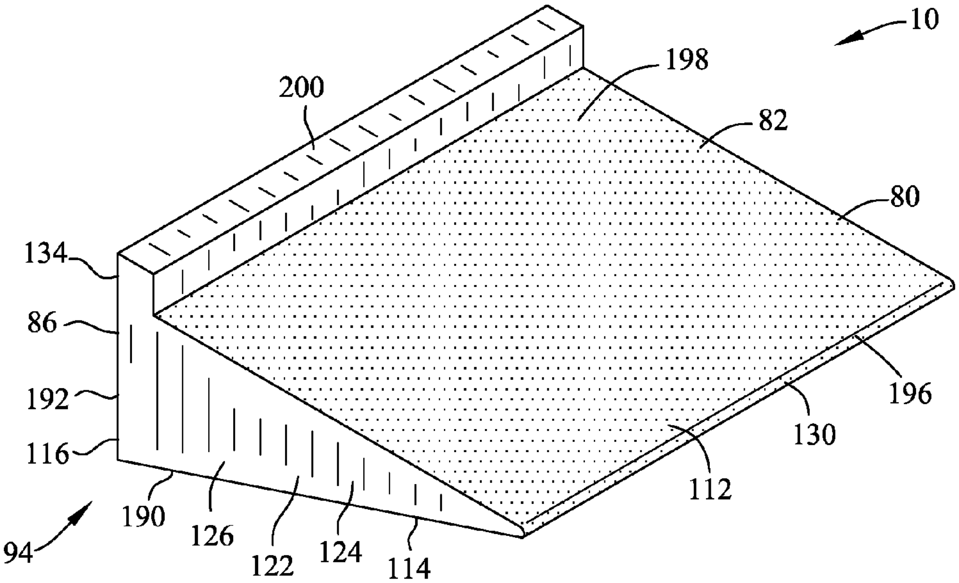
FIG. 14 is a bottom isometric of FIG. 13.

As shown in FIGS. 13 and 14, the support body 80 may include a polymeric layer 198 coupled to the base plane surface 112 for increasing the coefficient of friction between the base plane surface 112 and the generally horizontal surface 64 and resisting displacement of the support body 80 relative to the support surface 60. The polymeric layer 198 may be secured to the support body 80 by an adhesive, hook and loop or other coupling means.

As shown in FIGS. 1-8, 11, 13-15 and 17, the support body 80 may include a braking body 200 extending from the base plane surface 112 for positioning adjacent to the generally vertical surface 66 of the support surface 60 for preventing a horizontal displacement of the support body 80 relative to the support surface 60.

Figure 15:
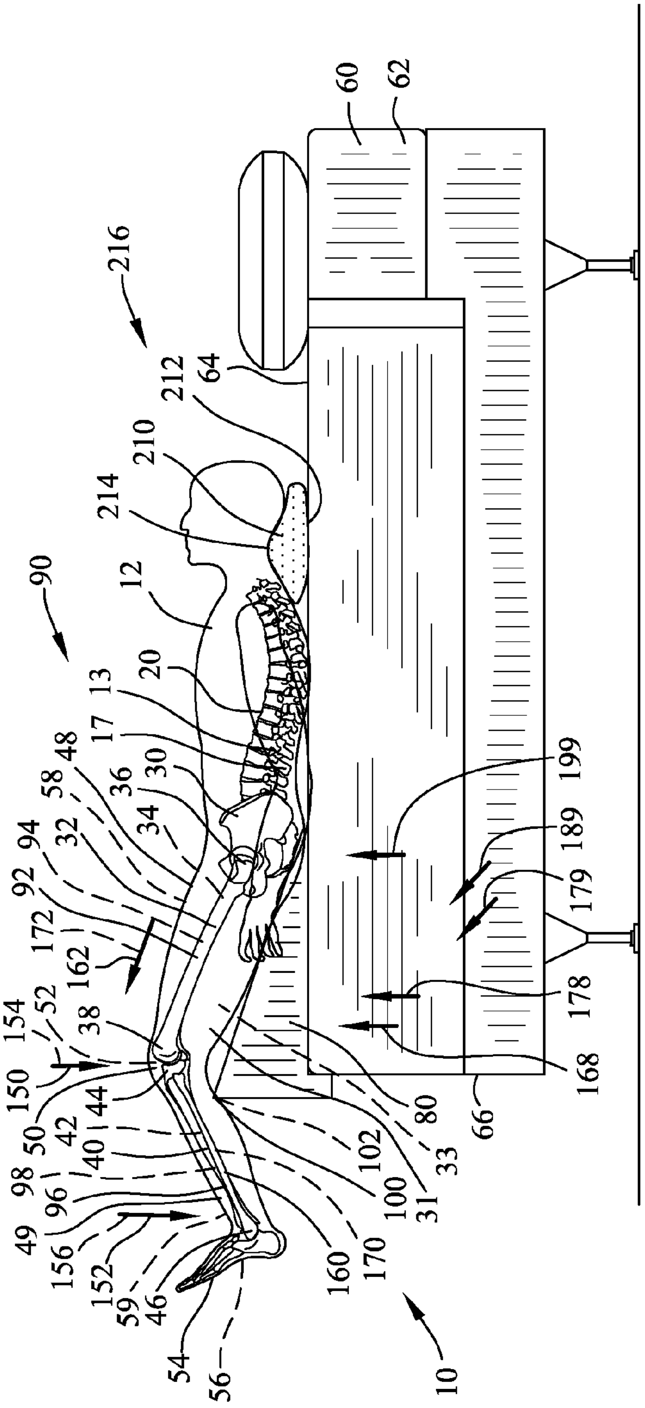
FIG. 15 is a view similar to FIG. 8 with an individual lying on the support surface body and utilizing vertebral column traction device of FIG. 13 along with a pillow body positioned between the support surface and an upper column end of the vertebral column.
Figure 16:
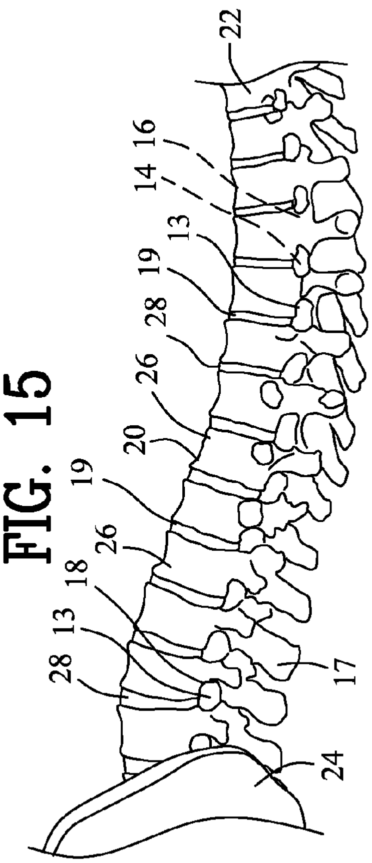
FIG. 16 is an enlarge view of a portion of FIG. 15 illustrating an expanded vertebral column.

As shown in FIGS. 15 and 16, the vertebral column traction device 10 may further include a pillow body 210. The pillow body 210 includes a base face 212 and an upper face 214. The base face 212 is adjacent to the generally horizontal surface 64 and the upper face 214 is generally adjacent to the upper column end 22 for positioning the upper column end 22 in an elevated orientation 216. The elevated orientation 216 isolates the expansion of the vertebral column 20 between the upper column end 22 and the lower column end 24.

FIGS. 21-24 illustrate a third embodiment 240 of the vertebral column traction device 10. More specifically, the third embodiment 240 includes the support body 80 being constructed from a first closed foam 242. The first closed foam 242 has a first foam density 244. The first closed foam 244 may be constructed from a polyurethane foam product having a grade 1845.

A front surface groove 250 is positioned on the front surface 84 and adjacent to the pivot area 88. A rear surface groove 252 is positioned on the rear surface 86 and adjacent to the pivot area 88. The first surface groove 250 and the rear surface groove 252 are continuous and have equivalent lengths for forming a generally V-shaped notch 254 within the support body 80. The generally V-shaped notch 254 receives a supplemental support layer 260 including a supplemental front layer 262 and a supplemental rear layer 264. The supplemental front layer 262 and a supplemental rear layer 264 may be constructed an integral one piece unit 266 having the equivalent length for forming a generally V-shaped cross-section 268.

The supplemental front layer 262 is positioned within the front surface groove 250 for defining a linear front surface 270 relative to the inclined plane surface 114 and the supplemental front layer 262. The supplemental rear layer 264 is positioned within the rear surface groove 252 for defining a linear rear surface 272 relative to the rear plane surface 116 and the supplemental rear layer 264. The supplemental support layer 260 may be secured within the generally V-shaped notch 254 by an adhesive, heat treatment or other securing means.

The supplemental front layer 262 coupling with the supplemental rear layer 264 defines a supplemental pivot area 274. The supplemental support layer 260 is constructed from a second closed foam 276 which has a second foam density 278. Preferably, the second foam density 278 is less than the first foam density 244 for permitting an increased displacement of the supplemental support layer 260 for increasing the surface area 280 between the first femur and the second femur and the vertebral column traction device 10 for increased comfort and preventing body circulation problems. In addition, the supplemental pivot area 274 may include a sharp curve radius 284 for further increasing comfort and preventing body circulation problems. The sharp curve radius 284 may include a one inch radius. More specifically, the second closed foam 276 may be constructed from a memory foam 282.

FIGS. 25-28 illustrate a fourth embodiment 300 of the vertebral column traction device 10. More specifically, the fourth embodiment 300 includes the support body 80 being constructed from a first closed foam 302. The first closed foam 302 has a first foam density 304. The first closed foam 302 may be constructed from a polyurethane foam product having a grade 1845.

A front surface groove 310 is positioned on the front surface 84 and adjacent to the pivot area 88. A rear surface groove 312 is positioned on the rear surface 86 and adjacent to the pivot area 88. The first surface groove 310 and the rear surface groove 312 are continuous and have non-equivalent lengths for forming a generally J-shaped notch 314 within the support body 80. More specifically, the rear surface groove 312 includes a rear height 316 and the front surface groove 310 includes a front length 318 defining a three to one length ratio 319 respectively.

The generally J-shaped notch 314 receives a supplemental support layer 320 including a supplemental front layer 322 and a supplemental rear layer 324. The supplemental front layer 322 and a supplemental rear layer 324 may be constructed an integral one piece unit 326 and have non-equivalent lengths for forming a generally J-shaped cross-section 328. More specifically, the supplemental rear layer 324 includes a rear height 325 and the supplemental front layer 322 includes a front length 323 defining a three to one length ratio 319 respectively.

The supplemental front layer 322 is positioned within the front surface groove 310 for defining a linear front surface 330 relative to the inclined plane surface 114 and the supplemental front layer 322. The supplemental rear layer 324 is positioned within the rear surface groove 312 for defining a linear rear surface 332 relative to the rear plane surface 116 and the supplemental rear layer 324. The supplemental support layer 320 may be secured within the generally J-shaped notch 314 by an adhesive, heat treatment or other securing means.

The supplemental front layer 322 coupling with the supplemental rear layer 324 defines a supplemental pivot area 334. The supplemental support layer 320 is constructed from a second closed foam 336 which has a second foam density 338. Preferably, the second foam density 338 is less than the first foam density 304 for permitting an increased displacement of the supplemental support layer 320 for increasing the surface area 340 between the first femur and the second femur and the vertebral column traction device 10 for increased comfort and preventing body circulation problems. In addition, the supplemental pivot area 334 may include a sharp curve radius 344 for further increasing comfort and preventing body circulation problems. The sharp curve radius 344 may include a one inch radius. More specifically, the second closed foam 336 may be constructed from a memory foam 342.

FIGS. 29-32, FIGS. 33-36 and FIGS. 37-40 illustrate a fifth embodiment 350, sixth embodiment 352 and a seventh embodiment 354 of the vertebral column traction device 10 respectively. The fifth embodiment 350, sixth embodiment 352 and a seventh embodiment 354 include the support body 80 being constructed from a first closed foam 360. The first closed foam 360 has a first foam density 362. The first closed foam 360 may be constructed from a polyurethane foam product having a grade 1845.

A front surface recess 364 is positioned on the front surface 84 and adjacent to the pivot area 88. A rear surface recess 366 is positioned on the rear surface 86 and adjacent to the pivot area 88. The first surface recess 364 and the rear surface recess 366 are continuous for defining a compound recess 368 located within the pivot area 88.

In FIGS. 29-32 and FIGS. 33-36, the compound recess 368 defines a recessed equal step 370. In FIGS. 37-40, the compound recess 368 defines a recessed non-equal step 372. The compound recess 368 receives a supplemental support layer 374 including a supplemental front layer 376 and a supplemental rear layer 378. The supplemental front layer 376 and a supplemental rear layer 378 may be constructed an integral one piece unit 380.

The supplemental front layer 376 is positioned within the front surface recess 364 for defining a linear front surface 382 relative to the inclined plane surface 114 and the supplemental front layer 376. The supplemental rear layer 378 is positioned within the rear surface recess 366 for defining a linear rear surface 384 relative to the rear plane surface 116 and the supplemental rear layer 378. The supplemental support layer 374 may be secured within the compound recess 368 by an adhesive, heat treatment or other securing means.

The supplemental front layer 376 coupling with the supplemental rear layer 378 defines a supplemental pivot area 386. The supplemental support layer 374 is constructed from a second closed foam 388 which has a second foam density 390. Preferably, the second foam density 390 is less than the first foam density 362 for permitting an increased displacement of the supplemental support layer 374 for increasing the surface area 392 between the first femur and the second femur and the vertebral column traction device 10 for increased comfort and preventing body circulation problems. More specifically, the second closed foam 388 may be constructed from a memory foam 394. In FIGS. 29-32 and 37-40, supplemental pivot area 386 includes an acute angle 396. In FIGS. 33-40, the supplemental pivot area 334 may include a sharp curve radius 398 for further increasing comfort and preventing body circulation problems. The sharp curve radius 398 may include a one inch radius.

FIGS. 41-44 illustrate an eighth embodiment 410 of the vertebral column traction device 10. More specifically, the eighth embodiment 410 includes the support body 80 being constructed from a first closed foam 412. The first closed foam 412 has a first foam density 414. The first closed foam 412 may be constructed from a polyurethane foam product having a grade 1845.

A supplemental support layer 420 includes a supplemental front layer 422 and a supplemental rear layer 424. The supplemental front layer 422 and a supplemental rear layer 424 may be constructed an integral one piece unit 426 having the equivalent length for forming a generally V-shaped cross-section 428.

The supplemental front layer 422 is positioned above the inclined plane surface 114 for defining a non-linear front surface 430 relative to the inclined plane surface 114 and the supplemental front layer 422. The supplemental rear layer 424 is positioned above the rear plane surface 116 for defining a non-linear rear surface 432 relative to the rear plane surface 116 and the supplemental rear layer 424. The supplemental support layer 420 may be secured to the support body 80 by an adhesive, heat treatment or other securing means.

The supplemental front layer 422 coupling with the supplemental rear layer 424 defines a supplemental pivot area 434. The supplemental support layer 420 is constructed from a second closed foam 436 which has a second foam density 438. Preferably, the second foam density 438 is less than the first foam density 414 for permitting an increased displacement of the supplemental support layer 420 for increasing the surface area 440 between the first femur and the second femur and the vertebral column traction device 10 for increased comfort and preventing body circulation problems. In addition, the supplemental pivot area 434 may include a sharp curve radius 442 for further increasing comfort and preventing body circulation problems. The sharp curve radius 442 may include a one inch radius. More specifically, the second closed foam 436 may be constructed from a memory foam 444.

FIGS. 45-48 illustrate a ninth embodiment 450 of the vertebral column traction device 10. More specifically, the ninth embodiment 450 includes the support body 80 being constructed from a first closed foam 452. The first closed foam 452 has a first foam density 454. The first closed foam 452 may be constructed from a polyurethane foam product having a grade 1845.

A supplemental support layer 460 including a supplemental front layer 462 and a supplemental rear layer 464. The supplemental front layer 462 and a supplemental rear layer 464 may be constructed an integral one piece unit 466 and have non-equivalent lengths for forming a generally J-shaped cross-section 468. More specifically, the supplemental rear layer 464 includes a rear height 470 and the supplemental front layer 462 includes a front length 472 defining a three to one length ratio 474 respectively.

The supplemental front layer 462 is positioned above the inclined plane surface 114 for defining a non-linear front surface 476 relative to the inclined plane surface 114 and the supplemental front layer 462. The supplemental rear layer 464 is positioned above the rear plane surface 116 for defining a non-linear rear surface 478 relative to the rear plane surface 116 and the supplemental rear layer 464. The supplemental support layer 460 may be secured to the support body 80 by an adhesive, heat treatment or other securing means.

The supplemental front layer 462 coupling with the supplemental rear layer 464 defines a supplemental pivot area 480. The supplemental support layer 460 constructed from a second closed foam 482 which has a second foam density 484. Preferably, the second foam density 484 is less than the first foam density 454 for permitting an increased displacement of the supplemental support layer 460 for increasing the surface area 486 between the first femur and the second femur and the vertebral column traction device 10 for increased comfort and preventing body circulation problems. In addition, the supplemental pivot area 480 may include a sharp curve radius 488 for further increasing comfort and preventing body circulation problems. The sharp curve radius 488 may include a one inch radius. More specifically, the second closed foam 482 may be constructed from a memory foam 490.

FIGS. 49-52 illustrates a tenth embodiment 500 of the vertebral column traction device 10. More specifically, the tenth embodiment 500 includes the support body 80 being constructed from a first closed foam 502. The first closed foam 502 has a first foam density 504. The first closed foam 502 may be constructed from a polyurethane foam product having a grade 1845.

A supplemental support layer 510 includes a supplemental front layer 512 and a supplemental rear layer 514. The supplemental front layer 512 and a supplemental rear layer 514 may be constructed an integral one piece unit 516 having the equivalent length and defining a mirror image for forming a generally arch shaped cross-section 518. The generally arch shaped cross-section 518 defines a broad curve radius 442. The broad curve radius 519 may include a three inch radius. The broad curve radius 519 increases the surface area 530 between the first femur and the second femur and the vertebral column traction device 10 for increased comfort and preventing body circulation problems. In addition, the pivot area 88 may include a sharp curve radius 532 consistently supporting the broad curve radius 519. The sharp curve radius 532 may include a one inch radius.

The supplemental front layer 512 is positioned above the inclined plane surface 114 for defining a non-linear front surface 520 relative to the inclined plane surface 114 and the supplemental front layer 512. The supplemental rear layer 514 is positioned above the rear plane surface 116 for defining a non-linear rear surface 522 relative to the rear plane surface 116 and the supplemental rear layer 514. The supplemental support layer 510 may be secured to the support body 80 by an adhesive, heat treatment or other securing means.

The supplemental front layer 512 coupling with the supplemental rear layer 514 defines a supplemental pivot area 524. The supplemental support layer 510 is constructed from a second closed foam 526 which has a second foam density 528. Preferably, the second foam density 528 is less than the first foam density 504 for permitting an increased displacement of the supplemental support layer 510 for increasing the surface area 530 between the first femur and the second femur and the vertebral column traction device 10 for increased comfort and preventing body circulation problems. In addition, the supplemental pivot area 524 may include a broad curve radius 519 for further increasing comfort and preventing body circulation problems. The broad curve radius 519 may include a three inch radius. More specifically, the second closed foam 526 may be constructed from a memory foam 534.

FIGS. 53-64 illustrate the vertebral column traction device 10 having a curve radius 540 positioned on the pivot area 88. The curve radius 540 may include a one inch radius. The curve radius 540 increases the surface area 542 between the first femur and the second femur and the vertebral column traction device 10 for increased comfort and preventing body circulation problems.

FIGS. 53-56 illustrates an eleventh embodiment of the vertebral column traction device 10. The base surface 82 has a base length 550 equivalent to 20.4 inches and a base width 552 equivalent to 24 inches. The front surface 84 has a front length 554 equivalent to 18.7 inches and a front width 556 equivalent to 24 inches. The rear surface 86 has a rear height 560 equivalent to 8.6 inches and a rear width 562 equivalent to 24 inches. The curve radius is equivalent to a 1 inches radius.

Figure 59:
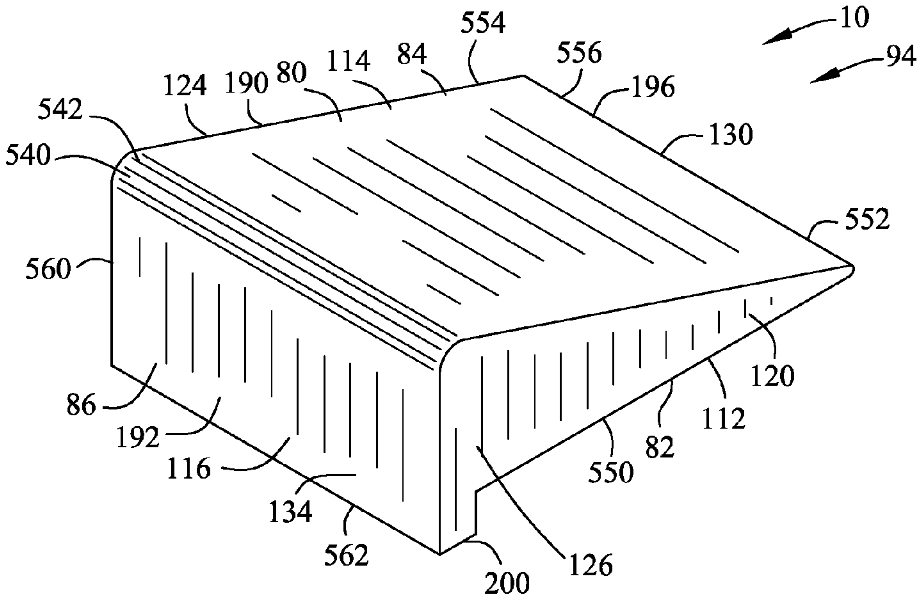
FIG. 59 is a top isometric view of a twelfth embodiment of the vertebral column traction device for expanding the vertebral column of an individual wherein the pivot area includes a curve radius and having a first alternative dimensional set.

FIG. 59 illustrates a twelfth embodiment of the vertebral column traction device 10. The base surface 82 has a base length 550 equivalent to 20.5 inches and a base width 552 equivalent to 18 inches. The front surface 84 has a front length 554 equivalent to 18.8 inches and a front width 556 equivalent to 18 inches. The rear surface 86 has a rear height 560 equivalent to 8.6 inches and a rear width 562 equivalent to 18 inches. The curve radius is equivalent to a 1 inches radius.

Figure 60:
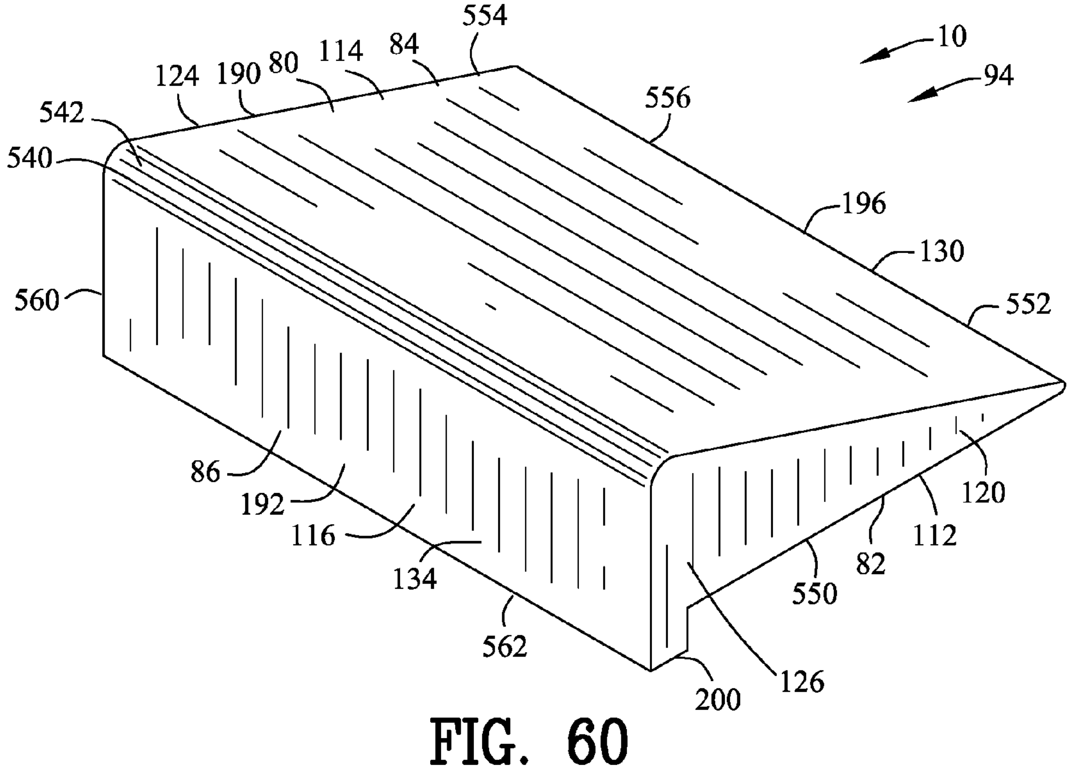
FIG. 60 is a top isometric view of a thirtieth embodiment of the vertebral column traction device for expanding the vertebral column of an individual wherein the pivot area includes a curve radius and having a second alternative dimensional set.

FIG. 60 illustrates a thirteenth embodiment of the vertebral column traction device 10. The base surface 82 has a base length 550 equivalent to 20.7 inches and a base width 552 equivalent to 30 inches. The front surface 84 has a front length 554 equivalent to 18.8 inches and a front width 556 equivalent to 30 inches. The rear surface 86 has a rear height 560 equivalent to 8.6 inches and a rear width 562 equivalent to 30 inches. The curve radius is equivalent to a 1 inches radius.

Figure 61:
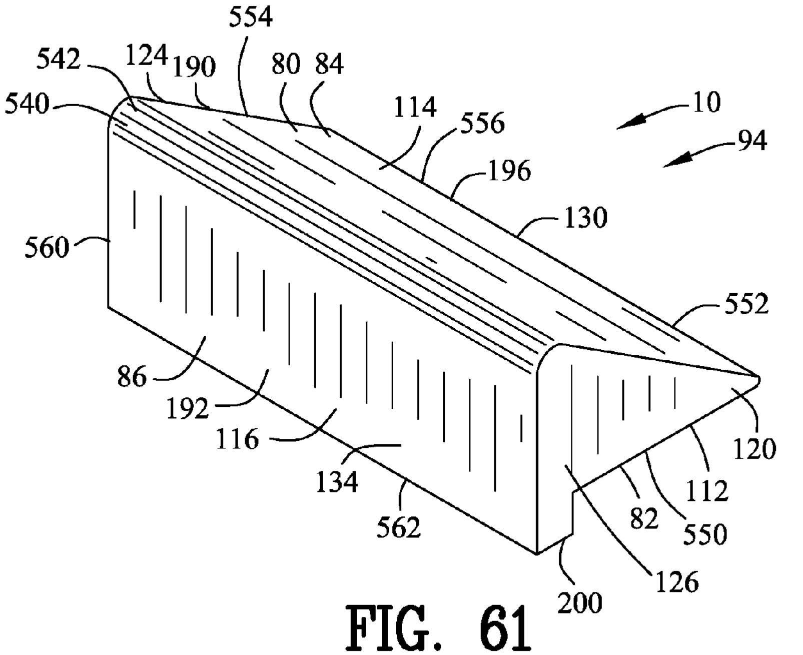
FIG. 61 is a top isometric view of a fortieth embodiment of the vertebral column traction device for expanding the vertebral column of an individual wherein the pivot area includes a curve radius and having a third alternative dimensional set.

FIG. 61 illustrates a fourteenth embodiment of the vertebral column traction device 10. The base surface 82 has a base length 550 equivalent to 10.5 inches and a base width 552 equivalent to 24 inches. The front surface 84 has a front length 554 equivalent to 9.6 inches and a front width 556 equivalent to 24 inches. The rear surface 86 has a rear height 560 equivalent to 8.6 inches and a rear width 562 equivalent to 24 inches. The curve radius is equivalent to a 1 inches radius.

Figure 62:
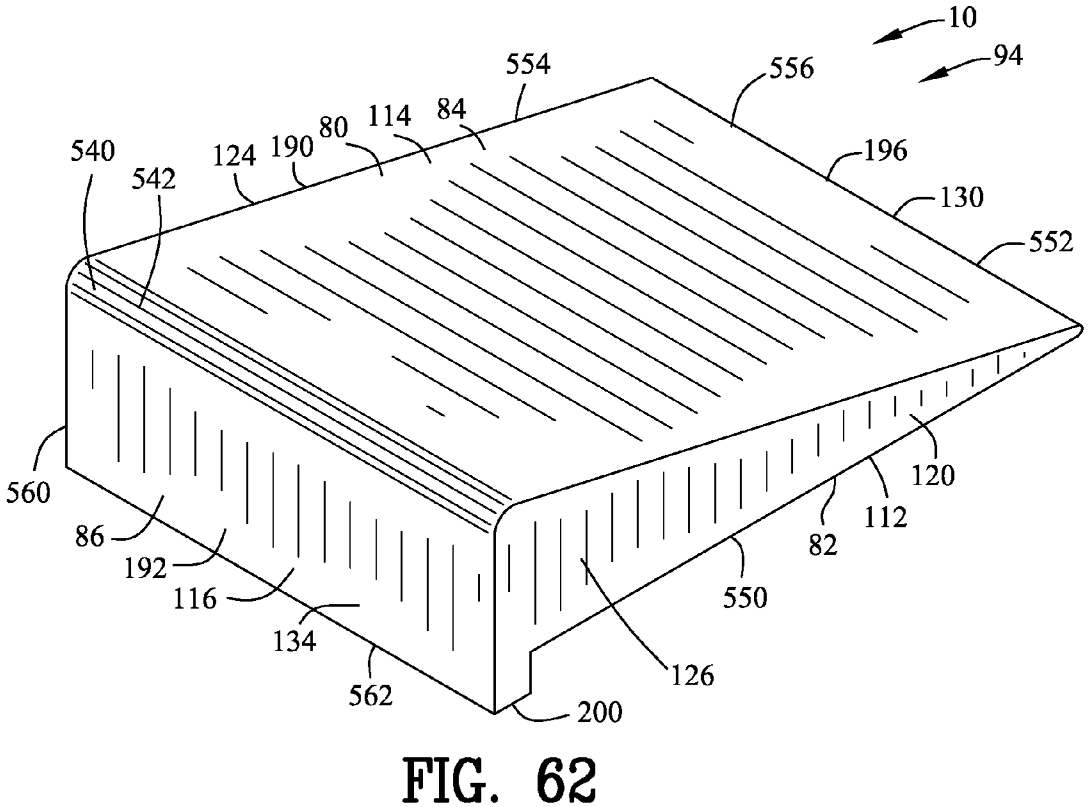
FIG. 62 is a top isometric view of a fiftieth embodiment of the vertebral column traction device for expanding the vertebral column of an individual wherein the pivot area includes a curve radius and having a fourth alternative dimensional set.

FIG. 62 illustrates a fifteenth embodiment of the vertebral column traction device 10. The base surface 82 has a base length 550 equivalent to 31 inches and a base width 552 equivalent to 24 inches. The front surface 84 has a front length 554 equivalent to 28.6 inches and a front width 556 equivalent to 24 inches. The rear surface 86 has a rear height 560 equivalent to 8.6 inches and a rear width 562 equivalent to 24 inches. The curve radius is equivalent to a 1 inches radius.

Figure 63:
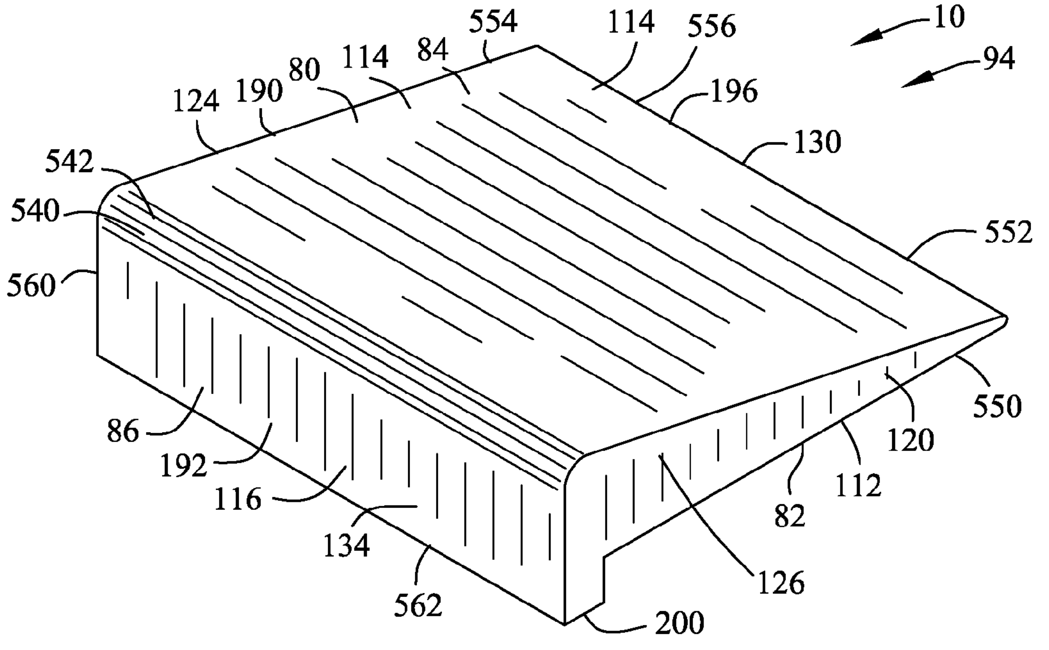
FIG. 63 is a top isometric view of a sixtieth embodiment of the vertebral column traction device for expanding the vertebral column of an individual wherein the pivot area includes a curve radius and having a fifth alternative dimensional set.

FIG. 63 illustrates a sixteenth embodiment of the vertebral column traction device 10. The base surface 82 has a base length 550 equivalent to 20.6 inches and a base width 552 equivalent to 24 inches. The front surface 84 has a front length 554 equivalent to 19.5 inches and a front width 556 equivalent to 24 inches. The rear surface 86 has a rear height 560 equivalent to 6 inches and a rear width 562 equivalent to 24 inches. The curve radius equivalent to a 1 inches radius.

Figure 64:
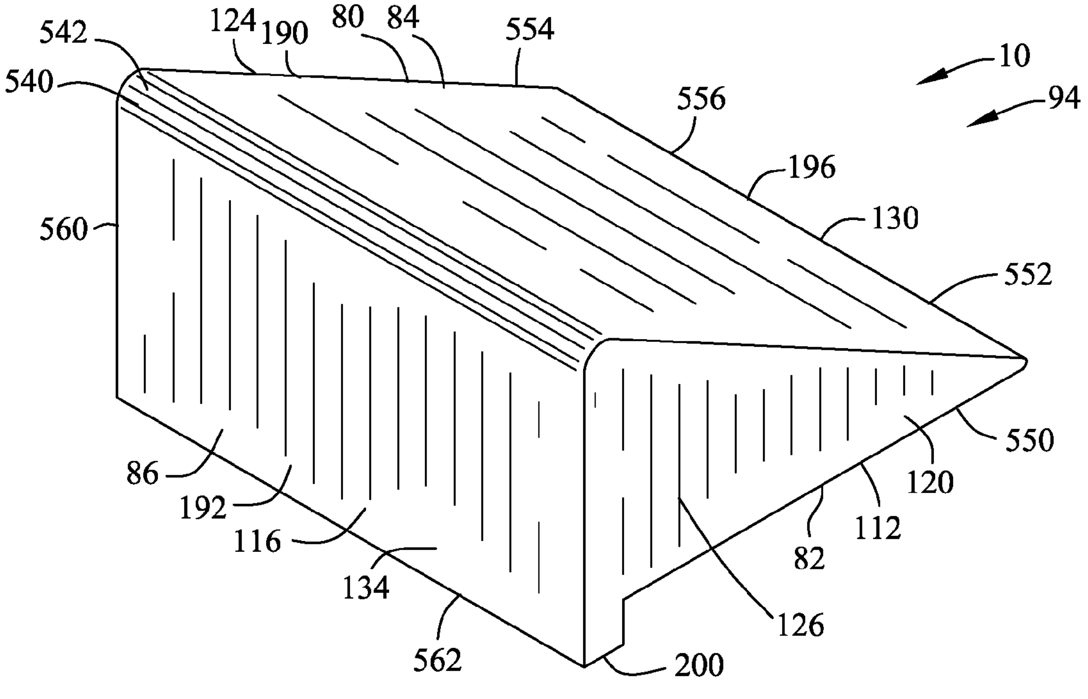
FIG. 64 is a top isometric view of a seventieth embodiment of the vertebral column traction device for expanding the vertebral column of an individual wherein the pivot area includes a curve radius and having a sixth alternative dimensional set.

FIG. 64 illustrates a seventeenth embodiment of the vertebral column traction device 10. The base surface 82 has a base length 550 equivalent to 20.5 inches and a base width 552 equivalent to 24 inches. The front surface 84 has a front length 554 equivalent to 18.5 inches and a front width 556 equivalent to 24 inches. The rear surface 86 has a rear height 560 equivalent to 13 inches and a rear width 562 equivalent to 24 inches. The curve radius equivalent to a 1 inches radius.

The present invention further incorporates a method for expanding the vertebral column 20 of an individual 12. The method comprises the steps of positioning a generally shaped wedge support body (124, 80) adjacent to a generally horizontal surface 64 and in proximity with a generally vertical surface 66 of a support surface 60. A first femur 32 and a second femur 34 are positioned adjacent to an inclined plane surface 114 of the generally shaped wedge support body (124, 80) for placing the first femur 32 and the second femur 34 in a first inclined orientation 92 and a second inclined orientation 94 respectively. A first tibia 40 and a second tibia 42 are positioned so that there is a distance between the first tibia 40 and the second tibia 42 from a riser plane surface 116 of the generally shaped wedge support body (124, 80) for positioning the first tibia 40 and the second tibia 42 in a first cantilever orientation 96 and a second cantilever orientation 98 respectively. The first tibia 40 and the second tibia 42 are positioned adjacent to a vertex 132 between the inclined plane surface 114 and the riser plane surface 116 for pivoting the first tibia 40 and the second tibia 42 on the vertex 132 for defining a first fulcrum 100 and a second fulcrum 102 respectively. A first lever 160 is created about the first fulcrum 100. A second lever 170 is created about the second fulcrum 102. A primary mechanical advantage output force 162 is generated by the first lever 160 and is conveyed from the first femur 32, through the pelvis 30 and to the vertebral column 20 for expanding the vertebral column 20 of an individual 12. A secondary mechanical advantage output force 172 is generated by the second lever 170 and is conveyed from the second femur 34, through the pelvis 30 and to the vertebral column 20 for expanding the vertebral column 20 of an individual 12.

A further step in the method for expanding the vertebral column 20 of an individual 12 further comprises the step of coupling a first supplementary weight 180 to the first tibia 40 or the first foot 54 for increasing the primary mechanical advantage output force (162, 184) to further expand the vertebral column 20 of the individual 12. A second supplementary weight 182 is coupled to the second tibia 42 or the second foot 56 for increasing the secondary mechanical advantage output force (172, 186) to further expand the vertebral column 20 of the individual 12.

A further step in the method for expanding the vertebral column 20 of an individual 12 further comprises the step of positioning a pillow body 210 adjacent to a generally horizontal surface 64 and adjacent to an upper column end 22 for isolating the expansion of the vertebral column 20 between the upper column end 22 and a lower column end 24.

Theory of Operation

We believe the benefits of the vertebral column traction device 10 can best be understood in the terms of two cycles. First is the daily cycle of rest and activity. When the body is at rest, especially horizontally, the plurality of intervertebral discs 28 have a normal supply of spinal fluid to keep them healthy and of normal size. When the body is vertical and engaging in normal movements, the plurality of intervertebral discs 28 are under pressure and some of the spinal fluid in the plurality of intervertebral discs 28 is squeezed out into the spinal canal 16. The plurality of intervertebral discs 28 have several component parts, such as the nucleus pulposus, the annulus and tissue such as fascia which keep much of the fluid, but not all of it, in the plurality of intervertebral discs 28. When the body is at rest, spinal fluid pressure tends to equalize in the spinal canal 16, allowing the plurality of intervertebral discs 28 to become rehydrated and to regain its more normal healthy size.

We believe the function of the vertebral column traction device 10 is to facilitate and make more effective the normal regenerating processes of the body, through the mechanism of gentle traction or stretching the low back. When this gentle traction or stretching occurs, a slight relative vacuum is created in the space between the plurality of vertebrae 26 affirmatively drawing into the intervertebral disc 28 the fluid necessary to nourish it by rehydrating the plurality of intervertebral discs 28 and maintaining its normal healthy condition, and helping to restore it to its normal size.

We believe the vertebral column traction device 10 is especially suited to this function, since it is essentially a pillow, has no moving parts, and can be used in bed before sleep, and simply and conveniently moved off the bed when the body is ready to sleep. We believe the vertebral column traction device 10 therefore hastens, facilitates, and makes more effective the body's normal restorative activity during sleep.

As evidence of this function, it is commonly known that a person is slightly taller in the morning than in the evening, reflecting the restoration of the more normal health and maintenance of the disc during sleep, and its later diminution in size during the day.

We believe the second cycle to which reference may be useful in understanding the function of the vertebral column traction device 10, is the general life cycle of youth and age. As the body ages, it is commonly observed that height is lost and people actually become shorter. A large component in this process is believed to be the intervertebral discs 28, repeatedly losing their mass through continued compression and dehydration, which in time becomes their normal condition. This is commonly referred to in radiological or x-ray reports as "desiccation" or drying out of the discs 28, and spinal "stenosis" meaning a narrowing of the spaces 19 between the vertebrae 26.

By the processes described above, we believe the vertebral column traction device 10 can ameliorate and delay and hopefully prevent to a large degree the progressive degeneration of the discs 28 and relative loss of height, and accompanying pain in the low back and legs often requiring surgical intervention. It may be noted that several popular surgical techniques and practices involve specifically enlarging the foramen 13 through surgery which is expensive, painful, time-consuming, and entirely antithetical to the current public efforts to reduce health care costs. We believe by using the vertebral column traction device 10 for a relatively short time, such as a half-hour, while lying in bed before sleep, much back and leg pain, and loss of normal function and maintenance of the back can be avoided.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A device for supporting a portion of an individual, a support surface having a generally horizontal surface and a generally vertical surface for engaging the device, the device, comprising:

a support body including a base surface, a front surface and a rear surface;

said front surface intersecting said rear surface for defining a pivot area;

said front surface defining an inclined orientation adapted to support the portion of the individual;

said base surface of said support body including a base plane surface;

said front surface of said support body including an inclined plane surface;

said rear surface of said support body including a riser plane surface;

a first triangle plane surface and a second triangle plane surface intersect said base plane surface, said inclined plane surface and said riser plane surface for defining a generally shaped wedge; and a braking body extending from said base surface for positioning adjacent to the generally vertical surface of the support surface for preventing a horizontal displacement of said support body relative to the support surface.

2. A device for supporting a portion of an individual as set forth in claim 1, wherein said first triangle plane surface and said second triangle plane surface shaped in the form of a right triangle.

3. A device for supporting a portion of an individual as set forth in claim 2, wherein said front surface including an inclined length;

said rear surface including a riser length; and said inclined length being greater than said riser length for further defining said generally shaped wedge.

4. A device for supporting a portion of an individual as set forth in claim 1, wherein said support body is construction of a closed foam.

5. A device for supporting a portion of an individual as set forth in claim 1, further including a polymeric layer coupled to said base surface for increasing the coefficient of friction between said base surface and the generally horizontal surface and resisting displacement of said support body relative to the support surface.

6. A vertebral column traction device for expanding the vertebral column of an individual, the vertebral column extending between an upper column end and a lower column end, a pelvis is coupled to the lower column end of the vertebral column, a first femur and a second femur extend between a proximal end and a distal end, the proximal end of the first femur and the second femur are coupled to the pelvis, a first tibia and a second tibia extend between a proximal end and a distal end, the proximal end of the first tibia and the second tibia are coupled to the distal end of the first femur and the second femur by a first knee joint and a second knee joint respectively, a first foot and a second foot are coupled to the distal end of the first tibia and the second tibia respectively, a support surface having a generally horizontal surface for supporting a portion of the individual and a generally vertical surface for extending a portion of the individual beyond the support surface, the vertebral column traction device, comprising:

a support body including a base plane surface, an inclined plane surface, a riser plane surface, a first triangle plane surface and a second triangle plane surface for defining a generally shaped wedge;

said base plane surface intersecting said inclined plane surface for defining a first vertex;

said inclined plane surface intersecting said riser plane surface for defining a second vertex;

said riser plane surface intersecting said base plane surface for defining a third vertex;

said base plane surface adjacent to the generally horizontal surface and said riser plane surface in proximity with the generally vertical surface of the support surface for defining an operation position of said support body;

said inclined plane surface defining an inclined orientation adapted to support the first femur and the second femur;

said second vertex defining a pivot area adapted to support the first tibia and the second tibia and extending the first foot and the second foot beyond the general horizontal surface of the support surface;

said inclined orientation and said pivot area expanding the vertebral column of the individual;

a braking body extending from said base plane surface for positioning adjacent to the generally vertical surface of the support surface for preventing a horizontal displacement of said support body relative to the support surface.

7. A vertebral column traction device for expanding the vertebral column of an individual as set forth in claim 6, wherein said first triangle plane surface and said second triangle plane surface shaped in the form of a right triangle.

8. A vertebral column traction device for expanding the vertebral column of an individual as set forth in claim 7, wherein said front surface including an inclined length;

said rear surface including a riser length; and said inclined length being greater than said riser length for further defining said generally shaped wedge.

9. A vertebral column traction device for expanding the vertebral column of an individual as set forth in claim 6, wherein said support body is construction of a closed foam.

10. A vertebral column traction device for expanding the vertebral column of an individual as set forth in claim 6, further including a polymeric layer coupled to said base plane surface for increasing the coefficient of friction between said base plane surface and the generally horizontal surface and resisting displacement of said support body relative to the support surface.

11. A vertebral column traction device for expanding the vertebral column of an individual as set forth in claim 6, further including a first supplementary weight adapted to couple to the first tibia or the first foot for increasing the expansion of the vertebral column of the individual; and a second supplementary weight adapted to couple to the second tibia or the second foot for increasing the expansion of the vertebral column of the individual.

12. A vertebral column traction device for expanding the vertebral column of an individual as set forth in claim 6, further including a pillow body including a base face and an upper face;

said base face adjacent to the generally horizontal surface and said upper face generally adjacent to the upper column end for positioning the upper column end in an elevated orientation; and said elevated orientation isolating the expansion of the vertebral column between the upper column end and the lower column end.

13. A vertebral column traction device for expanding the vertebral column of an individual, the vertebral column extending between an upper column end and a lower column end, the vertebral column includes a plurality of vertebrae separated by a plurality of intervertebral discs, a pelvis is coupled to the lower column end of the vertebral column, a first femur and a second femur extend between a proximal end and a distal end, the proximal end of the first femur and the second femur are coupled to the pelvis, a first tibia and a second tibia extend between a proximal end and a distal end, the proximal end of the first tibia and the second tibia are coupled to the distal end of the first femur and the second femur by a first knee joint and a second knee joint respectively, a first foot and a second foot are coupled to the distal end of the first tibia and the second tibia respectively, a support surface having a generally horizontal surface for supporting a portion of the individual and a generally vertical surface for extending a portion of the individual beyond the support surface, the vertebral column traction device, comprising:

- a support body including a base surface, a front surface and a rear surface;
- said front surface intersecting said rear surface for defining a pivot area;
- said base surface of said support body including a base plane surface;
- said front surface of said support body including an inclined plane surface;
- said rear surface of said support body including a riser plane surface;
- a first triangle plane surface and a second triangle plane surface intersect said base plane surface, said inclined plane surface and said riser plane surface for defining a generally shaped wedge;
- said base plane surface adjacent to the generally horizontal surface and said riser plane surface in proximity with the generally vertical surface of the support surface for defining an operation position of said support body;
- said inclined plane surface defining an inclined orientation adapted to support the first femur and the second femur;
- said pivot area supporting the first tibia and the second tibia and extending the first foot and the second foot beyond the general horizontal surface of the support surface;
- said inclined orientation and said pivot area expanding the vertebral column of the individual;
- said support body is construction of a first closed foam having a first foam density;
- a front surface groove positioned on said front surface and adjacent to said pivot area;
- a rear surface groove positioned on said rear surface and adjacent to said pivot area;
- a supplemental support layer including a supplemental front layer and a supplemental rear layer;
- said supplemental front layer positioned within said front surface groove for defining a linear front surface;
- said supplemental rear layer positioned within said rear surface groove for defining a linear rear surface;
- said supplemental front layer coupling with said supplemental rear layer for defining a supplemental pivot area;
- said supplemental support layer constructed from a second closed foam and having a second foam density; and
- said second foam density being less than said first foam density for permitting an increased displacement of the supplemental support layer for increasing the surface area between the first femur and the second femur for increased comfort.

14. A vertebral column traction device for expanding the vertebral column of an individual as set forth in claim 13, wherein said supplemental pivot area includes a sharp curve radius.

15. A vertebral column traction device for expanding the vertebral column of an individual as set forth in claim 13, wherein said supplemental pivot area includes a broad curve radius.

16. A vertebral column traction device for expanding the vertebral column of an individual as set forth in claim 13, wherein said supplemental front layer includes a supplemental front length;

- said supplemental rear layer includes a supplemental rear length; and
- said supplemental rear length and said supplemental front length defining a three to one length ratio respectively.

17. A vertebral column traction device for expanding the vertebral column of an individual, the vertebral column extending between an upper column end and a lower column end, the vertebral column includes a plurality of vertebrae separated by a plurality of intervertebral discs, a pelvis is coupled to the lower column end of the vertebral column, a first femur and a second femur extend between a proximal end and a distal end, the proximal end of the first femur and the second femur are coupled to the pelvis, a first tibia and a second tibia extend between a proximal end and a distal end, the proximal end of the first tibia and the second tibia are coupled to the distal end of the first femur and the second femur by a first knee joint and a second knee joint respectively, a first foot and a second foot are coupled to the distal end of the first tibia and the second tibia respectively, a support surface having a generally horizontal surface for supporting a portion of the individual and a generally vertical surface for extending a portion of the individual beyond the support surface, the vertebral column traction device, comprising:

- a support body including a base surface, a front surface and a rear surface;
- said front surface intersecting said rear surface for defining a pivot area;
- said base surface of said support body including a base plane surface;
- said front surface of said support body including an inclined plane surface;
- said rear surface of said support body including a riser plane surface;
- a first triangle plane surface and a second triangle plane surface intersect said base plane surface, said inclined plane surface and said riser plane surface for defining a generally shaped wedge;
- said base plane surface adjacent to the generally horizontal surface and said riser plane surface in proximity with the generally vertical surface of the support surface for defining an operation position of said support body;
- said inclined plane surface defining an inclined orientation adapted to support the first femur and the second femur;
- said pivot area adapted to support the first tibia and the second tibia and extending the first foot and the second foot beyond the general horizontal surface of the support surface;
- said inclined orientation and said pivot area expanding the vertebral column of the individual;
- said support body is construction of a first closed foam having a first foam density;

a supplemental support layer including a supplemental front layer and a supplemental rear layer;

said supplemental front layer positioned on said front surface and adjacent to said pivot area;

said supplemental rear layer positioned on said rear surface and adjacent to said pivot area;

said supplemental front layer coupling with said supplemental rear layer for defining a supplemental pivot area;

said supplemental support layer constructed from a second closed foam and having a second foam density; and said second foam density being less than said first foam density for permitting an increased displacement of the supplemental support layer for increasing the surface area between the first femur and the second femur for increased comfort.

18. A vertebral column traction device for expanding the vertebral column of an individual as set forth in claim 17, wherein said supplemental pivot area includes a sharp curve radius.

19. A vertebral column traction device for expanding the vertebral column of an individual as set forth in claim 17, wherein said supplemental pivot area includes a broad curve radius.

20. A vertebral column traction device for expanding the vertebral column of an individual as set forth in claim 17, wherein said supplemental front layer includes a supplemental front length;

said supplemental rear layer includes a supplemental rear length; and said supplemental rear length and said supplemental front length defining a three to one length ratio respectively.

* * * * *